(12) United States Patent
Turner et al.

(10) Patent No.: US 11,903,655 B2
(45) Date of Patent: Feb. 20, 2024

(54) SYSTEMS AND METHODS FOR SPINAL CORRECTION SURGICAL PLANNING

(71) Applicant: NuVasive, Inc., San Diego, CA (US)

(72) Inventors: Alex Turner, San Diego, CA (US); Jeffrey Harris, San Diego, CA (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 18/087,948

(22) Filed: Dec. 23, 2022

(65) Prior Publication Data

US 2023/0130184 A1 Apr. 27, 2023

Related U.S. Application Data

(63) Continuation of application No. 17/206,256, filed on Mar. 19, 2021, now Pat. No. 11,576,727, which is a
(Continued)

(51) Int. Cl.
*A61B 34/10* (2016.01)
*G16H 50/50* (2018.01)
(Continued)

(52) U.S. Cl.
CPC .............. *A61B 34/10* (2016.02); *G06N 5/04* (2013.01); *G16H 50/50* (2018.01);
(Continued)

(58) Field of Classification Search
CPC .............. A61B 34/10; A61B 2034/104; A61B 2034/105; A61B 2034/107;
(Continued)

(56) References Cited

U.S. PATENT DOCUMENTS

| 2,693,798 A | 11/1954 | Haboush |
| 3,866,458 A | 2/1975 | Wagner |
| (Continued) | | |

FOREIGN PATENT DOCUMENTS

| CA | 2826947 | 3/2014 |
| CN | 2885154 | 4/2007 |
| (Continued) | | |

OTHER PUBLICATIONS

AnyBody Publication List, located online on Sep. 29, 2022 at: https://anybodytech.com/resources/anybodypublications/, 90 pages.
(Continued)

*Primary Examiner* — Bitew A Dinke

(57) ABSTRACT

A system for surgical planning and assessment of spinal deformity correction is provided that has a spinal imaging system and a control unit. The spinal imaging system is configured to collect at least one digitized position of one or more vertebral bodies of a subject. The control unit is configured to receive the at least one digitized position, and calculate, based on the at least one digitized position, an optimized posture for the subject. The control unit is configured to receive one or more simulated spinal correction inputs, and based on the inputs and optimized posture, predict an optimal simulated postoperative surgical correction.

20 Claims, 12 Drawing Sheets

Related U.S. Application Data continuation of application No. 16/582,760, filed on Sep. 25, 2019, now Pat. No. 10,987,169, which is a continuation of application No. 15/448,119, filed on Mar. 2, 2017, now Pat. No. 10,463,433.

(60) Provisional application No. 62/302,725, filed on Mar. 2, 2016.

(51) Int. Cl.
  *G06N 5/04* (2023.01)
  *A61F 2/44* (2006.01)
  *A61F 2/30* (2006.01)

(52) U.S. Cl.
  CPC ... *A61B 2034/104* (2016.02); *A61B 2034/105* (2016.02); *A61B 2034/107* (2016.02); *A61B 2034/108* (2016.02); *A61F 2/30942* (2013.01); *A61F 2/44* (2013.01); *A61F 2/4455* (2013.01); *G06T 2207/30012* (2013.01)

(58) Field of Classification Search
  CPC .... A61B 2034/108; G06N 5/04; G16H 50/50; A61F 2/30942; A61F 2/44; A61F 2/4455; G06T 2207/30012
  See application file for complete search history.

(56) References Cited

U.S. PATENT DOCUMENTS

| | | | |
|---|---|---|---|
| 4,409,968 A | 10/1983 | Drummond | |
| 4,411,259 A | 10/1983 | Drummond | |
| 4,474,046 A | 10/1984 | Cook | |
| 4,653,481 A | 3/1987 | Howland et al. | |
| 4,773,402 A | 9/1988 | Asher | |
| 4,887,595 A | 12/1989 | Heinig et al. | |
| 5,099,846 A | 3/1992 | Hardy | |
| 5,113,685 A | 5/1992 | Asher et al. | |
| 5,161,404 A | 11/1992 | Hayes | |
| 5,239,716 A | 8/1993 | Fisk | |
| 5,271,382 A | 12/1993 | Chikama | |
| 5,290,289 A | 3/1994 | Sanders et al. | |
| 5,389,099 A | 2/1995 | Hartmeister et al. | |
| 5,490,409 A | 2/1996 | Weber | |
| 5,548,985 A | 8/1996 | Yapp | |
| 5,564,302 A | 10/1996 | Watrous | |
| 5,591,165 A | 1/1997 | Jackson | |
| 5,658,286 A | 8/1997 | Sava | |
| 5,672,175 A * | 9/1997 | Martin | A61B 17/7044 606/279 |
| 5,704,937 A | 1/1998 | Martin | |
| 5,740,802 A | 4/1998 | Nafis et al. | |
| 5,765,561 A | 6/1998 | Chen et al. | |
| 5,799,055 A | 8/1998 | Peshkin et al. | |
| 5,819,571 A | 10/1998 | Johnson | |
| 5,819,580 A | 10/1998 | Gauthier | |
| 5,880,976 A | 3/1999 | DiGioia, III | |
| D415,665 S | 10/1999 | Nordell, II et al. | |
| 6,006,581 A | 12/1999 | Holmes | |
| 6,015,409 A | 1/2000 | Jackson | |
| 6,024,759 A | 2/2000 | Nuss et al. | |
| 6,035,691 A | 3/2000 | Lin et al. | |
| 6,128,944 A | 10/2000 | Haynes | |
| 6,205,411 B1 | 3/2001 | DiGioia, III et al. | |
| 6,226,548 B1 | 5/2001 | Foley | |
| 6,264,658 B1 | 7/2001 | Lee et al. | |
| 6,285,902 B1 | 9/2001 | Kienzle, III | |
| 6,327,491 B1 | 12/2001 | Franklin et al. | |
| 6,332,780 B1 | 12/2001 | Traxel et al. | |
| 6,529,765 B1 | 3/2003 | Franck | |
| 6,592,585 B2 | 7/2003 | Lee et al. | |
| 6,596,008 B1 | 7/2003 | Kambin | |
| 6,644,087 B1 | 11/2003 | Ralph et al. | |
| 6,701,174 B1 | 3/2004 | Krause | |
| 6,711,432 B1 | 3/2004 | Krause | |
| 7,346,382 B2 | 3/2008 | McIntyre et al. | |
| 7,454,939 B2 | 11/2008 | Garner et al. | |
| 7,488,331 B2 | 2/2009 | Abdelgany | |
| 7,634,306 B2 | 12/2009 | Sarin et al. | |
| RE42,226 E | 3/2011 | Foley et al. | |
| 7,957,831 B2 | 6/2011 | Isaacs | |
| 8,101,116 B2 | 1/2012 | Lindh, Sr. et al. | |
| 8,126,736 B2 | 2/2012 | Anderson et al. | |
| 8,177,843 B2 | 5/2012 | Schalliol | |
| 8,235,998 B2 | 8/2012 | Miller et al. | |
| 8,255,045 B2 | 8/2012 | Gharib et al. | |
| 8,298,242 B2 | 10/2012 | Justis et al. | |
| 8,374,673 B2 | 2/2013 | Adcox et al. | |
| 8,442,621 B2 | 5/2013 | Gorek et al. | |
| 8,459,050 B2 | 6/2013 | Wilcox et al. | |
| 8,506,603 B2 | 8/2013 | McClintock et al. | |
| 8,549,888 B2 | 10/2013 | Isaacs | |
| 8,607,603 B2 | 12/2013 | Justis et al. | |
| 8,668,699 B2 | 3/2014 | Thomas et al. | |
| 8,714,427 B2 | 5/2014 | McClintock et al. | |
| 8,744,826 B2 | 6/2014 | Skalli et al. | |
| 8,753,346 B2 | 6/2014 | Suarez et al. | |
| 8,770,006 B2 | 7/2014 | Harper | |
| 8,831,324 B2 | 9/2014 | Penenberg | |
| 8,885,899 B2 | 11/2014 | Illes et al. | |
| 8,951,258 B2 | 2/2015 | Peultier | |
| 8,983,813 B2 | 3/2015 | Miles et al. | |
| 8,992,542 B2 | 3/2015 | Hagag et al. | |
| 9,119,670 B2 | 9/2015 | Yang et al. | |
| 9,129,054 B2 | 9/2015 | Nawana et al. | |
| 9,204,937 B2 | 12/2015 | Edelhauser et al. | |
| 9,211,145 B2 | 12/2015 | Pereiro de Lamo et al. | |
| 9,233,001 B2 | 1/2016 | Miles et al. | |
| 9,248,002 B2 | 2/2016 | McCarthy | |
| 9,320,604 B2 | 4/2016 | Miles et al. | |
| 9,408,698 B2 | 8/2016 | Miles et al. | |
| 9,452,050 B2 | 9/2016 | Miles et al. | |
| 9,572,682 B2 | 2/2017 | Aghazadeh | |
| 9,597,157 B2 | 3/2017 | Hagag et al. | |
| 9,662,228 B2 | 5/2017 | McCarthy | |
| 9,700,292 B2 | 7/2017 | Nawana et al. | |
| 9,724,167 B2 | 8/2017 | Ziaei et al. | |
| 9,757,072 B1 | 9/2017 | Urbalejo | |
| 9,785,246 B2 | 10/2017 | Isaacs | |
| 9,861,446 B2 | 1/2018 | Lang | |
| 9,877,847 B2 | 1/2018 | Bettenga | |
| 9,962,166 B1 | 5/2018 | Sachs et al. | |
| 9,968,408 B1 * | 5/2018 | Casey | A61B 34/10 |
| 10,139,920 B2 | 11/2018 | Isaacs | |
| 10,188,480 B2 | 1/2019 | Scholl | |
| 10,420,480 B1 * | 9/2019 | Schermerhorn | A61B 5/24 |
| 10,444,855 B2 | 10/2019 | Isaacs | |
| 10,463,433 B2 * | 11/2019 | Turner | G16H 50/50 |
| 10,507,060 B2 | 12/2019 | Casey et al. | |
| 10,507,061 B2 | 12/2019 | Casey et al. | |
| 10,684,697 B2 | 6/2020 | Isaacs | |
| 10,695,099 B2 | 6/2020 | Scholl | |
| 10,709,509 B2 | 7/2020 | Scholl | |
| 10,987,169 B2 * | 4/2021 | Turner | A61B 34/10 |
| 11,107,586 B1 * | 8/2021 | DeCook | G16H 30/00 |
| 11,207,132 B2 | 12/2021 | Isaacs | |
| 11,207,136 B2 | 12/2021 | Casey et al. | |
| 11,229,493 B2 | 1/2022 | Finley | |
| 11,231,787 B2 | 1/2022 | Isaacs | |
| 11,376,045 B2 | 7/2022 | Scholl | |
| 11,576,727 B2 * | 2/2023 | Turner | A61B 34/10 |
| 2002/0107573 A1 | 8/2002 | Steinberg | |
| 2003/0055435 A1 | 3/2003 | Barrick | |
| 2003/0055502 A1 | 3/2003 | Lang | |
| 2003/0060824 A1 | 3/2003 | Viart et al. | |
| 2004/0044295 A1 | 3/2004 | Reinart et al. | |
| 2004/0068187 A1 | 4/2004 | Krause | |
| 2004/0087962 A1 | 5/2004 | Gorek | |
| 2004/0097952 A1 | 5/2004 | Sarin | |
| 2004/0144149 A1 | 7/2004 | Strippgen et al. | |
| 2004/0147927 A1 | 7/2004 | Tsougarakis | |
| 2004/0152972 A1 | 8/2004 | Hunter | |
| 2005/0043660 A1 | 2/2005 | Stark et al. | |

(56) References Cited

U.S. PATENT DOCUMENTS

| | | |
|---|---|---|
| 2005/0054917 A1 | 3/2005 | Kitson |
| 2005/0119593 A1 | 6/2005 | Gallard et al. |
| 2005/0192575 A1 | 9/2005 | Pacheo |
| 2005/0203511 A1 | 9/2005 | Wilson-MacDonald et al. |
| 2005/0245817 A1 | 11/2005 | Clayton |
| 2005/0262911 A1 | 12/2005 | Dankowicz et al. |
| 2005/0288809 A1 | 12/2005 | Spaeth |
| 2006/0015030 A1 | 1/2006 | Poulin et al. |
| 2006/0082015 A1 | 4/2006 | Happonen et al. |
| 2006/0150698 A1 | 7/2006 | Garner et al. |
| 2006/0150699 A1 | 7/2006 | Garner et al. |
| 2006/0212158 A1 | 9/2006 | Miller |
| 2006/0235338 A1 | 10/2006 | Pacheco |
| 2006/0235427 A1 | 10/2006 | Thomas et al. |
| 2006/0264973 A1 | 11/2006 | Abdelgany |
| 2007/0073137 A1 | 3/2007 | Schoenefeld |
| 2007/0093689 A1 | 4/2007 | Steinberg |
| 2007/0118055 A1 | 5/2007 | McCombs |
| 2007/0172797 A1* | 7/2007 | Hada ................ G09B 23/32 434/1 |
| 2007/0174769 A1 | 7/2007 | Nycz |
| 2007/0227216 A1 | 10/2007 | Schalliol |
| 2007/0233079 A1 | 10/2007 | Fallin et al. |
| 2007/0269544 A1 | 11/2007 | Erickson et al. |
| 2007/0288064 A1 | 12/2007 | Butson et al. |
| 2008/0009945 A1 | 1/2008 | Pacheco |
| 2008/0039717 A1 | 2/2008 | Frigg |
| 2008/0103500 A1 | 5/2008 | Chao et al. |
| 2008/0161680 A1 | 7/2008 | von Jako |
| 2008/0177203 A1 | 7/2008 | von Jako |
| 2008/0212858 A1 | 9/2008 | Boese et al. |
| 2008/0262812 A1 | 10/2008 | Arata et al. |
| 2008/0269596 A1 | 10/2008 | Revie |
| 2008/0319275 A1 | 12/2008 | Chiu |
| 2009/0018808 A1 | 1/2009 | Bronstein |
| 2009/0024164 A1 | 1/2009 | Neubardt |
| 2009/0099605 A1 | 4/2009 | Fallin et al. |
| 2009/0118714 A1 | 5/2009 | Teodorescu |
| 2009/0132050 A1 | 5/2009 | Holm |
| 2009/0138020 A1 | 5/2009 | Park et al. |
| 2009/0157083 A1 | 6/2009 | Park |
| 2009/0222020 A1 | 9/2009 | Schmuck et al. |
| 2009/0226055 A1 | 9/2009 | Dankowicz et al. |
| 2009/0226068 A1 | 9/2009 | Fitz |
| 2009/0249851 A1 | 10/2009 | Isaacs |
| 2009/0254097 A1 | 10/2009 | Isaacs |
| 2009/0254326 A1 | 10/2009 | Isaacs |
| 2009/0276045 A1 | 11/2009 | Lang |
| 2009/0287271 A1 | 11/2009 | Blum et al. |
| 2009/0299477 A1 | 12/2009 | Clayton et al. |
| 2010/0030232 A1 | 2/2010 | Zehavi et al. |
| 2010/0042105 A1 | 2/2010 | Park et al. |
| 2010/0042154 A1 | 2/2010 | Biedermann et al. |
| 2010/0076563 A1 | 3/2010 | Otto et al. |
| 2010/0100011 A1 | 4/2010 | Roche |
| 2010/0101295 A1 | 4/2010 | Miller et al. |
| 2010/0111631 A1 | 5/2010 | Trieu et al. |
| 2010/0177948 A1 | 7/2010 | Le Bras |
| 2010/0183201 A1 | 7/2010 | Schwab et al. |
| 2010/0191071 A1 | 7/2010 | Anderson |
| 2010/0191100 A1 | 7/2010 | Anderson |
| 2010/0217109 A1 | 8/2010 | Belcher |
| 2010/0268119 A1 | 10/2010 | Morrison |
| 2010/0292963 A1 | 11/2010 | Schroeder |
| 2011/0040340 A1 | 2/2011 | Miller et al. |
| 2011/0054870 A1 | 3/2011 | Dariush et al. |
| 2011/0066193 A1 | 3/2011 | Lang |
| 2011/0071802 A1 | 3/2011 | Bojarski |
| 2011/0084108 A1 | 4/2011 | McClintock et al. |
| 2011/0093108 A1 | 4/2011 | Ashby et al. |
| 2011/0121049 A1 | 5/2011 | Malinouskas |
| 2011/0245871 A1 | 10/2011 | Williams |
| 2011/0253760 A1 | 10/2011 | McClintock et al. |
| 2011/0265538 A1 | 11/2011 | Trieu et al. |
| 2011/0270262 A1 | 11/2011 | Justis et al. |
| 2011/0295378 A1 | 12/2011 | Bojarski et al. |
| 2011/0305379 A1 | 12/2011 | Mahfouz |
| 2011/0319745 A1 | 12/2011 | Frey |
| 2012/0010710 A1 | 1/2012 | Frigg |
| 2012/0014580 A1 | 1/2012 | Blum |
| 2012/0035507 A1 | 2/2012 | George et al. |
| 2012/0041562 A1 | 2/2012 | Shachar et al. |
| 2012/0047980 A1 | 3/2012 | Harper |
| 2012/0116203 A1 | 5/2012 | Vancraen |
| 2012/0141034 A1 | 6/2012 | Iannotti et al. |
| 2012/0186411 A1 | 7/2012 | Lodahi et al. |
| 2012/0230573 A1 | 9/2012 | Ito et al. |
| 2012/0247173 A1 | 10/2012 | Paris et al. |
| 2012/0265268 A1 | 10/2012 | Blum |
| 2012/0274631 A1 | 11/2012 | Friedland |
| 2012/0289965 A1 | 11/2012 | Gelaude et al. |
| 2013/0053854 A1 | 2/2013 | Schoenefeld |
| 2013/0060130 A1 | 3/2013 | Park et al. |
| 2013/0072980 A1 | 3/2013 | Biedermann et al. |
| 2013/0072982 A1 | 3/2013 | Simonson |
| 2013/0091921 A1 | 4/2013 | Wilcox et al. |
| 2013/0096625 A1 | 4/2013 | McClintock et al. |
| 2013/0113791 A1 | 5/2013 | Isaacs |
| 2013/0123850 A1 | 5/2013 | Schoenefeld |
| 2013/0131480 A1 | 5/2013 | Ruhl |
| 2013/0131486 A1 | 5/2013 | Copf et al. |
| 2013/0144342 A1 | 6/2013 | Strauss et al. |
| 2013/0173240 A1 | 7/2013 | Koell et al. |
| 2013/0218163 A1 | 8/2013 | Frey |
| 2013/0296954 A1 | 11/2013 | Skaggs et al. |
| 2013/0303883 A1 | 11/2013 | Zehavi et al. |
| 2013/0304217 A1 | 11/2013 | Reeber et al. |
| 2013/0304429 A1 | 11/2013 | Haimerl |
| 2013/0307955 A1 | 11/2013 | Deitz et al. |
| 2013/0325069 A1* | 12/2013 | Pereiro de Lamo ........................ A61B 17/7049 606/264 |
| 2013/0345757 A1 | 12/2013 | Stad |
| 2014/0025118 A1 | 1/2014 | Fallin et al. |
| 2014/0031871 A1 | 1/2014 | Fallin et al. |
| 2014/0066994 A1 | 3/2014 | Dominik et al. |
| 2014/0076883 A1 | 3/2014 | Brailovski et al. |
| 2014/0081659 A1 | 3/2014 | Nawana |
| 2014/0100582 A1 | 4/2014 | Koch et al. |
| 2014/0135841 A1 | 5/2014 | Wallenstein |
| 2014/0135842 A1 | 5/2014 | Wallenstein |
| 2014/0135843 A1 | 5/2014 | Barrus |
| 2014/0135844 A1 | 5/2014 | Ark et al. |
| 2014/0137618 A1 | 5/2014 | Isaacs |
| 2014/0168121 A1 | 6/2014 | Chou |
| 2014/0188121 A1 | 7/2014 | Lavallee |
| 2014/0207197 A1 | 7/2014 | Reisberg |
| 2014/0240355 A1 | 8/2014 | Isaacs |
| 2014/0244220 A1* | 8/2014 | McKinnon ................ A61F 2/02 703/1 |
| 2014/0249591 A1 | 9/2014 | Peultier et al. |
| 2014/0260484 A1 | 9/2014 | Harper |
| 2014/0272881 A1 | 9/2014 | Barsoum |
| 2014/0275981 A1 | 9/2014 | Selover et al. |
| 2014/0278322 A1 | 9/2014 | Jaramaz |
| 2014/0284838 A1 | 9/2014 | Pfeffer et al. |
| 2014/0311203 A1 | 10/2014 | Crawford et al. |
| 2014/0364860 A1 | 12/2014 | Knoepfle et al. |
| 2014/0378828 A1 | 12/2014 | Penenberg et al. |
| 2015/0073265 A1 | 3/2015 | Popovic et al. |
| 2015/0100091 A1* | 4/2015 | Tohmeh ............ A61B 17/7083 606/279 |
| 2015/0150523 A1 | 6/2015 | Sirpad et al. |
| 2015/0157416 A1 | 6/2015 | Andersson |
| 2015/0216568 A1 | 8/2015 | Sanpera Trigueros et al. |
| 2015/0227679 A1 | 8/2015 | Kamer et al. |
| 2015/0238271 A1 | 8/2015 | Wollowick et al. |
| 2015/0282796 A1 | 10/2015 | Nawana et al. |
| 2015/0282797 A1* | 10/2015 | O'Neil ................ A61B 1/3135 606/279 |
| 2015/0328004 A1 | 11/2015 | Mafhouz |
| 2016/0100907 A1 | 4/2016 | Gomes |
| 2016/0117817 A1 | 4/2016 | Seel |
| 2016/0157751 A1 | 6/2016 | Mahfouz |

(56) References Cited

U.S. PATENT DOCUMENTS

| | | |
|---|---|---|
| 2016/0191887 A1 | 6/2016 | Casas |
| 2016/0210374 A1 | 7/2016 | Mosnier et al. |
| 2016/0220318 A1 | 8/2016 | Farardeau et al. |
| 2016/0235479 A1* | 8/2016 | Mosnier .................. A61B 34/10 |
| 2016/0235480 A1* | 8/2016 | Scholl ................ A61B 17/7083 |
| 2016/0242857 A1 | 8/2016 | Scholl |
| 2016/0262800 A1 | 9/2016 | Scholl et al. |
| 2016/0270772 A1* | 9/2016 | Beale ...................... A61B 17/70 |
| 2016/0296285 A1 | 10/2016 | Chaoui et al. |
| 2016/0354161 A1 | 12/2016 | Dietz |
| 2017/0071682 A1 | 3/2017 | Bar et al. |
| 2017/0119472 A1 | 5/2017 | Hermann et al. |
| 2017/0128145 A1 | 5/2017 | Hasser et al. |
| 2017/0135707 A9 | 5/2017 | Frey et al. |
| 2017/0135770 A1 | 5/2017 | Scholl |
| 2017/0165008 A1* | 6/2017 | Finley .................. A61B 6/5235 |
| 2017/0215857 A1 | 8/2017 | D'urso |
| 2017/0231710 A1* | 8/2017 | Scholl .................. A61B 5/7475 |
| | | 606/279 |
| 2017/0252107 A1 | 9/2017 | Turner et al. |
| 2017/0252123 A1 | 9/2017 | D'urso |
| 2017/0258526 A1 | 9/2017 | Lang |
| 2017/0360493 A1 | 12/2017 | Zucker et al. |
| 2017/0367738 A1 | 12/2017 | Scholl et al. |
| 2018/0008349 A1 | 1/2018 | Gillman |
| 2018/0092699 A1 | 4/2018 | Finley |
| 2018/0098715 A1 | 4/2018 | Dietz |
| 2018/0104479 A1 | 4/2018 | Grill et al. |
| 2018/0116727 A1 | 5/2018 | Caldwell et al. |
| 2018/0132942 A1 | 5/2018 | Mosnier et al. |
| 2018/0228566 A9 | 8/2018 | McAfee |
| 2018/0233222 A1 | 8/2018 | Daley et al. |
| 2018/0253838 A1 | 9/2018 | Sperling et al. |
| 2018/0254107 A1* | 9/2018 | Casey .................... A61B 34/10 |
| 2018/0263701 A1 | 9/2018 | Casey et al. |
| 2018/0301213 A1* | 10/2018 | Zehavi ...................... G06T 7/73 |
| 2018/0303552 A1 | 10/2018 | Ryan et al. |
| 2018/0310993 A1 | 11/2018 | Hobeika et al. |
| 2018/0368921 A1 | 12/2018 | Jeszenszky et al. |
| 2019/0029757 A1 | 1/2019 | Roh et al. |
| 2019/0046268 A1 | 2/2019 | Mosnier et al. |
| 2019/0046269 A1 | 2/2019 | Hedblom et al. |
| 2019/0069956 A1 | 3/2019 | Ryan et al. |
| 2019/0099221 A1 | 4/2019 | Schmidt et al. |
| 2019/0146458 A1 | 5/2019 | Roh et al. |
| 2019/0167435 A1 | 6/2019 | Cordonnier |
| 2019/0209212 A1 | 7/2019 | Scholl et al. |
| 2019/0216452 A1 | 7/2019 | Nawana et al. |
| 2019/0254750 A1 | 8/2019 | Metz |
| 2019/0254769 A1 | 8/2019 | Scholl et al. |
| 2019/0269459 A1 | 9/2019 | Mosnier et al. |
| 2019/0314094 A1 | 10/2019 | Crawford |
| 2019/0350657 A1 | 11/2019 | Tolkowsky |
| 2019/0362028 A1 | 11/2019 | Mosnier et al. |
| 2019/0380782 A1 | 12/2019 | McAfee et al. |
| 2019/0388099 A1 | 12/2019 | Zuhars et al. |
| 2020/0015857 A1 | 1/2020 | Rout et al. |
| 2020/0022758 A1 | 1/2020 | Shoham et al. |
| 2020/0038109 A1 | 2/2020 | Steinberg |
| 2020/0038111 A1 | 2/2020 | Turner et al. |
| 2020/0060768 A1 | 2/2020 | Mosnier et al. |
| 2020/0085503 A1 | 3/2020 | Casey et al. |
| 2020/0093542 A1 | 3/2020 | Arramon et al. |
| 2020/0093613 A1 | 3/2020 | Arramon et al. |
| 2020/0107883 A1 | 4/2020 | Herrmann et al. |
| 2020/0121394 A1 | 4/2020 | Mosnier et al. |
| 2020/0129217 A1 | 4/2020 | Zucker et al. |
| 2020/0129240 A1 | 4/2020 | Singh et al. |
| 2020/0138519 A1 | 5/2020 | Frey et al. |
| 2020/0155236 A1 | 5/2020 | Chi |
| 2020/0188026 A1 | 6/2020 | de Souza et al. |
| 2020/0197100 A1 | 6/2020 | Leung et al. |
| 2020/0202515 A1 | 6/2020 | Prasad et al. |
| 2020/0214854 A1 | 7/2020 | O'Grady |
| 2020/0222121 A1 | 7/2020 | Ignasiak |
| 2020/0261120 A1 | 8/2020 | Scholl |
| 2020/0268452 A1 | 8/2020 | Rezach et al. |
| 2020/0305985 A1 | 10/2020 | Tolkowsky |
| 2020/0311318 A1 | 10/2020 | Suddaby |
| 2020/0315708 A1 | 10/2020 | Mosnier et al. |
| 2020/0330160 A1 | 10/2020 | Dace et al. |
| 2020/0345420 A1 | 11/2020 | Hobeika et al. |
| 2020/0352651 A1 | 11/2020 | Junio et al. |
| 2020/0375636 A1 | 12/2020 | Hobeika et al. |
| 2020/0405397 A1 | 12/2020 | Liu et al. |
| 2020/0411163 A1 | 12/2020 | Zehavi et al. |
| 2021/0030443 A1 | 2/2021 | Scholl et al. |
| 2021/0038333 A1 | 2/2021 | Kostrzewski et al. |
| 2021/0059838 A1 | 3/2021 | Bodner |
| 2021/0093393 A1 | 4/2021 | Quist et al. |
| 2021/0145518 A1 | 5/2021 | Mosnier et al. |
| 2021/0145519 A1 | 5/2021 | Mosnier et al. |
| 2021/0153942 A1 | 5/2021 | Scheltienne et al. |
| 2021/0161682 A1 | 6/2021 | O'Neil et al. |
| 2021/0186615 A1 | 6/2021 | Shmayahu et al. |
| 2021/0210189 A1 | 7/2021 | Casey et al. |
| 2021/0212766 A1 | 7/2021 | Turner et al. |
| 2021/0216671 A1 | 7/2021 | Mosnier et al. |
| 2021/0244447 A1 | 8/2021 | Schroeder |
| 2021/0264601 A1 | 8/2021 | Pasha |
| 2021/0275227 A1 | 9/2021 | Park et al. |
| 2021/0298834 A1 | 9/2021 | Schlosser |
| 2021/0313062 A1 | 10/2021 | Junio |
| 2021/0315515 A1 | 10/2021 | Benson |
| 2021/0346092 A1 | 11/2021 | Redmond et al. |
| 2021/0346093 A1 | 11/2021 | Redmond et al. |
| 2022/0000556 A1 | 1/2022 | Casey et al. |
| 2022/0013211 A1 | 1/2022 | Steinberg et al. |
| 2022/0031396 A1 | 2/2022 | Ryan et al. |
| 2022/0071710 A1 | 3/2022 | Casey et al. |
| 2022/0096157 A1 | 3/2022 | Pollock et al. |
| 2022/0117754 A1 | 4/2022 | Sullivan et al. |
| 2022/0125602 A1 | 4/2022 | Zucker |
| 2022/0142709 A1 | 5/2022 | Zucker |
| 2022/0151699 A1 | 5/2022 | Schmidt et al. |
| 2022/0240986 A1 | 8/2022 | Scholl |

FOREIGN PATENT DOCUMENTS

| | | |
|---|---|---|
| CN | 200966629 | 10/2007 |
| CN | 101647724 | 2/2010 |
| CN | 202161397 | 3/2012 |
| CN | 202982181 | 6/2013 |
| CN | 107157579 | 9/2017 |
| CN | 107647914 | 2/2018 |
| CN | 109124763 A | 1/2019 |
| CN | 109124763 B | 9/2020 |
| DE | 9408154 | 7/1994 |
| DE | 29510041 | 10/1995 |
| DE | 29609276 | 8/1996 |
| DE | 10314882 | 10/2004 |
| DE | 102004008870 | 10/2004 |
| DE | 102007033219 | 1/2009 |
| DE | 102010033116 | 2/2012 |
| DE | 102011006574 | 10/2012 |
| DE | 202014100218 | 3/2014 |
| EP | 2017785 | 1/2009 |
| EP | 2153785 | 2/2010 |
| EP | 2468201 | 6/2012 |
| EP | 2522295 | 11/2012 |
| EP | 2730242 | 5/2014 |
| ES | 2401811 | 4/2013 |
| FR | 2975583 | 11/2012 |
| FR | 3004100 | 10/2014 |
| GB | 2267757 | 12/1993 |
| JP | H-04297270 | 10/1992 |
| JP | 2007213015 | 8/2007 |
| JP | 2007283081 | 11/2007 |
| JP | 2013230221 | 11/2013 |
| JP | 2015531661 | 11/2015 |
| JP | 2016093497 | 5/2016 |
| JP | 2016536051 | 11/2016 |
| PT | 103823 | 3/2009 |
| SU | 1747045 | 7/1992 |

(56) References Cited

FOREIGN PATENT DOCUMENTS

| | | |
|---|---|---|
| WO | 199808454 | 3/1998 |
| WO | 2007009263 | 1/2007 |
| WO | 2009035358 | 3/2009 |
| WO | 2009039371 | 3/2009 |
| WO | 2009140294 | 11/2009 |
| WO | 2011038845 | 4/2011 |
| WO | 2012062464 | 5/2012 |
| WO | 2012135653 | 10/2012 |
| WO | 2013070628 | 5/2013 |
| WO | 2013085982 | 6/2013 |
| WO | 2013150233 | 10/2013 |
| WO | 2014016824 | 1/2014 |
| WO | 2014043661 | 3/2014 |
| WO | 2014055081 | 4/2014 |
| WO | 2014074850 | 5/2014 |
| WO | 2014088801 | 6/2014 |
| WO | 2014107144 | 7/2014 |
| WO | 2014143762 | 9/2014 |
| WO | 2015054543 | 4/2015 |
| WO | 2015195843 | 12/2015 |
| WO | 2017064719 | 4/2017 |
| WO | 2017127838 | 7/2017 |
| WO | 2021160599 | 8/2021 |

OTHER PUBLICATIONS

AnyBody Technology, "ARO Medical breaks the degenerative spiral", ARO Medical, Version 1.3, Nov. 20, 2013, 1 page.

AnyScript.org—Wiki: AnyScript Support Wiki, Main Page, located online on the Wayback Machine on Sep. 29, 2022 at: https://web.archive.org/web/20160224235555/http://wiki.anyscript.org:80/index.php/Main_Page, page last modified Oct. 5, 2015, 2 pages.

Aubin et al., "Preoperative planning simulator for spinal deformity surgeries", Spine, 2008, pp. 2143-2152, 33, No. 20.

Aurouer et al., "Computerized preoperative planning for correction of sagittal deformity of the spine.", Surg Radiol Anat, 2009, pp. 781-792, 31, No. 10.

Australian Exam Report in Application 2017225796, dated Nov. 13, 2020, 5 pages.

Australian Exam Report in Application 2021203401, dated Jan. 7, 2022, 3 pages.

European Extended Search Report in Application 17760840.3, dated Sep. 30, 2019, 9 pages.

European Extended Search Report in Application 21168383.4, dated Jun. 28, 2021, 8 pages.

Farahani et al., "Prediction of the Movement Patterns for Human Squat Jumping Using the Inverse-Inverse Dynamics Technique", XIII International Symposium on Computer Simulation in Biomechanics, Jun. 30-Jul. 2, 2011, Leuven, Belgium, 2 pages.

Israeli Exam Report in Application 26132818, dated Jun. 14, 2021, 3 pages.

Japanese 2nd Written Opinion in Application 2018-545412, dated Jan. 17, 2022, 2 pages.

Japanese Decision of Refusal in Application 2018-545412, dated Jun. 7, 2022, 3 pages.

Japanese Notice of Reasons for Refusal in Application 2018-545412, dated Nov. 2, 2021, 6 pages.

Japanese Notice of Reasons for Refusal in Application 2018-545412, dated Mar. 2, 2021, 8 pages.

Japanese Search Report in Application 2018-545412, dated Feb. 15, 2021, 13 pages.

Japanese Written Opinion in Application 2018-545412, dated Jun. 1, 2021, 3 pages.

K2M Pre-Bent Rod Tool video, located online at: https://www.youtube.com/watch?v=GE-UqEOFXFk, duration 3:50, uploaded by Surgimap on Feb. 16, 2017, last accessed on Sep. 12, 2022, 1 page.

KEOPS Demonstration Video, located online at: https://www.youtube.com/watch?v=5f_SoE6Ze8g, duration 5:11, uploaded by SMAIO69 on Nov. 29, 2012, last accessed on Sep. 12, 2022, 1 page.

Lehman et al., "Do intraoperative radiographs in scoliosis surgery reflect radiographic result?", Clinical Orthopaedics and Related Research, 2010, pp. 679-686, 468, No. 2.

Majdouline et al., "Computer simulation for the optimization of Instrumentation strategies in adolescent idiopathic scoliosis.", Med Biol Eng Comput, 2009, pp. 1143-1154, 47, No. 11.

Medicrea UNiD Spinal Rod Used at Scoliosis and Spinal Surgery video, located online at: https://www.youtube.com/watch?v=E-MonYoKSEg, duration 1:58, uploaded by John Henry Krause Voice Actor on Jul. 28, 2015, last accessed on Sep. 12, 2022, 3 pages.

Metz, Lionel N., et al., Computer-Assisted Surgical Planning and Image-Guided Surgical Navigation in Refractory Adult Scoliosis Surgery, Spine vol. 33, No. 9, pp. E287-E292, 2008, Lippincott Williams & Wilkins.

PCT International Preliminary Report on Patentability in International Application PCT/US2017/020491, dated Sep. 13, 2018, 7 pages.

PCT International Search Report and Written Opinion in International Application PCT/US2017/020491, dated May 26, 2017, 10 pages.

Roussouly, Pierre et al., "Sagittal Parameters of the Spine: Biomechanical Approach", Eur. Spine J (Jul. 11, 2011); 20 (Suppl. 5):S578-S585.

Schlenk et al., "Biomechanics of spinal deformity", Neurosurgical Focus, 2003, 14, No. 1.

Smith et al., "Clinical and radiographic evaluation of the adult spinal deformity patient", Neurosurg Clin N Am, 2013, pp. 143-156, 24, No. 2.

Tanquay et al., "Relation between the sagittal pelvic and lumbar spine geometries following surgical correction of adolescent idiopathic scoliosis", European Spine Journal, 2007, pp. 531-536, 16, No. 4.

The NHS Innovations & EOS video, located online at: https://www.youtube.com/watch?v=GeU9kWcSY-I, duration 10:17, uploaded by EOS Imaging on Apr. 29, 2014, last accessed on Sep. 12, 2022, 9 pages.

\* cited by examiner

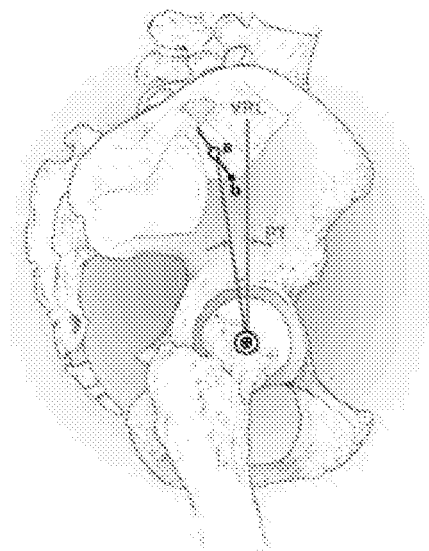 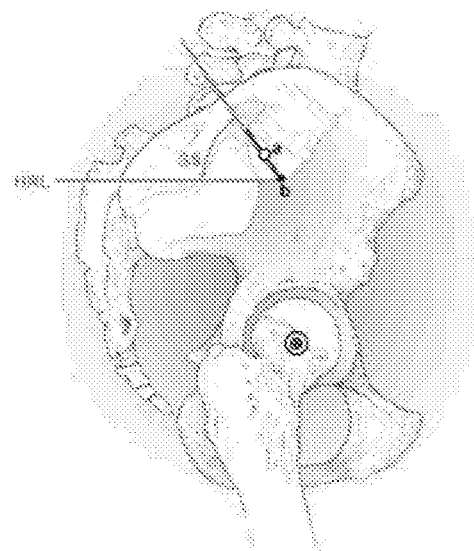
FIG. 7A    FIG. 7B
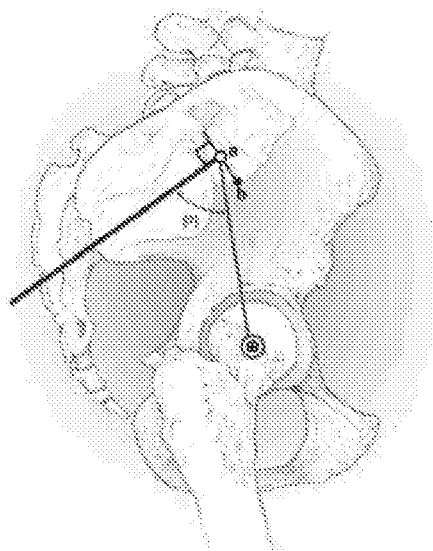
FIG. 7C

SYSTEMS AND METHODS FOR SPINAL CORRECTION SURGICAL PLANNING

CROSS REFERENCE TO RELATED APPLICATIONS

This application claims priority to and is a continuation of U.S. application Ser. No. 17/206,256, filed on Mar. 19, 2021, which is a continuation of U.S. application Ser. No. 16/582,760, filed on Sep. 25, 2019, now U.S. Pat. No. 10,987,169, which is a continuation of U.S. application Ser. No. 15/448,119, now U.S. Pat. No. 10,463,433, filed on Mar. 2, 2017, which claims the benefit of the priority date from U.S. Provisional Application No. 62/302,725, filed on Mar. 2, 2016, the entire contents of which are hereby expressly incorporated by reference into this disclosure as if set forth fully herein.

FIELD

The present disclosure relates generally to spinal surgery, more specifically to systems and methods relating to the planning, predicting, performing, and assessing of spinal deformity correction and compensatory changes. Such devices as well as systems and methods for use therewith are described.

BACKGROUND

The spinal column is a highly complex system of bones and connective tissues that provide support for the body and protect the delicate spinal cord and nerves. The spinal column includes a series of vertebral bodies stack atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the end plates of the upper and lower vertebrae are enclosed toward one another.

There are many types of spinal column disorders, including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, generative disc disease, fractured vertebrae, and the like).

Patients that suffer from such conditions often experience extreme and debilitating pain, as well as diminished nerve function. Posterior fixation for spinal fusions, decompression, deformity, and other reconstructions are performed to treat these patients. The aim of posterior fixation in lumbar, thoracic, and cervical procedures is to stabilize the spinal segments, correct multi-axis alignment, and aid in optimizing the long-term health of the spinal cord and nerves.

Spinal deformity is the result of structural change to the normal alignment of the spine and is usually due to at least one unstable motion segment. The definition and scope of spinal deformity, as well as treatment options, continues to evolve. Surgical objections for spinal deformity correction include curvature correction, prevention of further deformity, improvement or preservation of neurological function, and the restoration of sagittal and coronal balance. Sagittal plane alignment and parameters in cases of adult spinal deformity (ASD) are becoming increasingly recognized as correlative to health related quality of life score (HRQQL). In literature, there are significant correlations between HRQOL scores and radiographic parameters such as Sagittal Vertical Axis (SVA), Pelvic Tilt (PT) and mismatch between pelvic incidence and lumbar lordosis.

Spinal disorders, such as degenerative processes of the human spine, loss of disc height and lumbar kyphosis, result in a reduced HRQQL. The skeleton compensates for changes in the spine caused by these disorders to maintain balance and horizontal gaze of the subject. However, such compensation requires effort and energy from the subject and is correlated to a lower HRQQL score. Current surgical planning tools do not evaluate or include compensatory changes in a subject, leading to an undercorrection of a deformity in a patient that undergoes the surgical plan and procedure. Therefore, a need continues to exist for systems and methods that include compensatory changes as part of surgical planning.

SUMMARY

The needs described above, as well as others, are addressed by embodiments of a system for spinal correction surgical planning described in this disclosure (although it is to be understood that not all needs described above will necessarily be addressed by any one embodiment), as the system for spinal correction surgical planning of the present disclosure is separable into multiple pieces and can be used in methods, such as surgical planning methods. The systems of the present disclosure may be used, for example, in a method of increasing HRQQL in a subject.

In an aspect, a system for surgical planning and assessment of spinal deformity correction in a subject is provided. The system includes a spinal imaging system capable of collecting at least one digitized position, such as on a corner, of one or more vertebral bodies of the subject. In an embodiment, digitized positions are from two or more vertebral bodies. The system includes a control unit in communication with the spinal imaging system. The control unit is configured to receive the at least one digitized position of the one or more vertebral bodies. The control unit is configured to calculate, based on the at least one digitized position, an optimized posture for the subject. The calculation of the optimized posture of a subject may include processing a parametric study. The control unit is configured to receive one or more simulated spinal correction inputs, such as sagittal alignment, muscle recruitment criteria, or surgical procedure, such as intervertebral fusion. The control unit is configured to predict a simulated postoperative surgical correction based on the received one or more simulated spinal correction inputs and the received at least one digitized position of the one or more vertebral bodies. The control unit may be configured to determine, or suggest, a surgical plan based on the predicted simulated postoperative surgical correction. The prediction of simulated postoperative surgical correction may be based on one or more values selected from the group consisting of: knee flexion, pelvic retroversion, center of mass migration, ankle flexion, spinal compensation, and a combination thereof.

In some embodiments of the system, the control unit is configured to communicate the predicted simulated postoperative spinal correction to a user. The control unit may be configured to communicate, or output, a predicted simulated postoperative surgical correction, corresponding to a variance from the calculated optimized posture. The output value of less than 0 may represent a predicted undercorrection, and the output value of greater than 0 may represent an overcorrection. The at least one digitized position of the one or more vertebral bodies may be obtained from X-ray data, computed tomography imaging data, magnetic resonance imaging data, or biplanar X-ray data from the subject. These data may be taken from a patient who is in a lateral standing position.

In an embodiment of the system, the at least one digitized position is processed by the control unit to generate a musculoskeletal model of the subject. The processing of the at least one digitized position may include inverse-inverse dynamics modeling. The musculoskeletal model may include spinopelvic parameters, ligament parameters, joint kinematics, or any combination thereof. The spinopelvic parameters may include parameters selected from the group consisting of: pelvic tilt, sacral slope, pelvic incidence, sagittal vertical axis, lumbar lordosis, thoracic kyphosis, T1 pelvic angle, and combinations thereof. The musculoskeletal model may include muscle force data or muscle activation data. The control unit may be configured to compare the generated musculoskeletal model with predetermined musculoskeletal model data levels. Data from the generated musculoskeletal model, such as muscle force data or muscle activation data, may be communicated to a user.

In some embodiments of the system, the control unit is configured to generate a sagittal curvature profile based on the received at least one digitized position of the one or more vertebral bodies. The control unit may be configured to modify the musculoskeletal model data to match the sagittal curvature profile. The musculoskeletal model data may be modified by scaling, adjusting positioning of the one or more vertebral bodies, morphing a simulated subject anatomy, or combinations thereof.

In an embodiment of the system, the simulated postoperative surgical correction includes hip compensation, knee joint compensation, or ankle joint compensation. The prediction of a simulated postoperative surgical correction may also include a prediction of trunk muscle force output and leg muscle force output. The trunk muscle force output may include an erector spinae output, multifidi output, an obliques output, semispinalis output, an abdominal muscles output, or any combination thereof. The leg muscle force output includes a soleus output, a gastrocnemius output, a hip and knee flexors output, a hip and knee extensors output, a gluteus maximus output, a gluteus minimus output, or any combination thereof.

In some embodiments of the system, the simulated postoperative surgical correction includes simulating an implant in the subject.

In another aspect, a system for surgical planning and assessment of spinal deformity correction in a subject includes a spinal imaging system capable of collecting at least one digitized position of one or more vertebral bodies of the subject. The system includes a control unit configured to receive the at least one digitized position of the one or more vertebral bodies of the subject, and calculate, based on morphing and scaling the at least one digitized position onto a model, an optimized posture for the subject.

In yet another aspect, a system for surgical planning and providing a personalized implant for a subject includes a spinal imaging system capable of collecting at least one digitized position of one or more vertebral bodies of the subject. The system includes a control unit in communication with the spinal imaging system. The control unit is configured to receive the at least one digitized position of the one or more vertebral bodies of the subject to create an initial musculoskeletal model. The control unit is configured to calculate, based on the initial musculoskeletal model, an optimized posture for the subject. The control unit is configured to generate a simulated implant to change the initial musculoskeletal model towards the calculated optimized posture; and communicate dimensional data of the simulated implant to a user. The system may further comprise a three dimension printer configured to create at least part of the simulated implant.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIGS. 7A-7C illustrate bones in a pelvic region of a subject.

DETAILED DESCRIPTION

Illustrative embodiments of a system for surgical planning and assessment of spinal deformity correction are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system for surgical planning and assessment of spinal deformity correction in a subject and related systems and methods disclosed herein boast a variety of inventive features and components that warrant patent protection, both individually and in combination.

Values given here may be approximate (i.e., +/−20%, or 10%) such as to account for differences in surgical technique and patient-specific factors.

Figure 1:
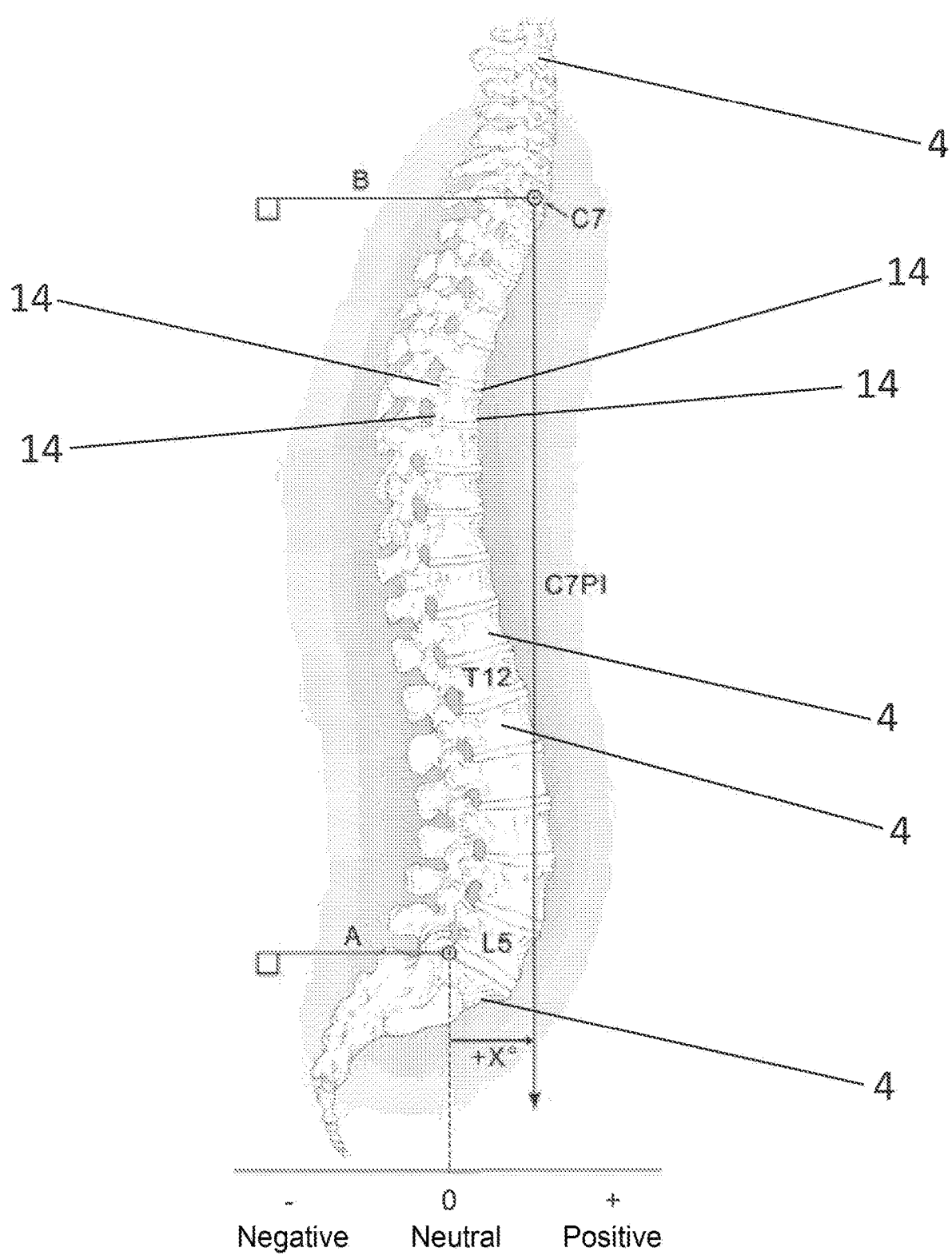
FIG. 1 is a side elevation view of a spine.
Figure 2:
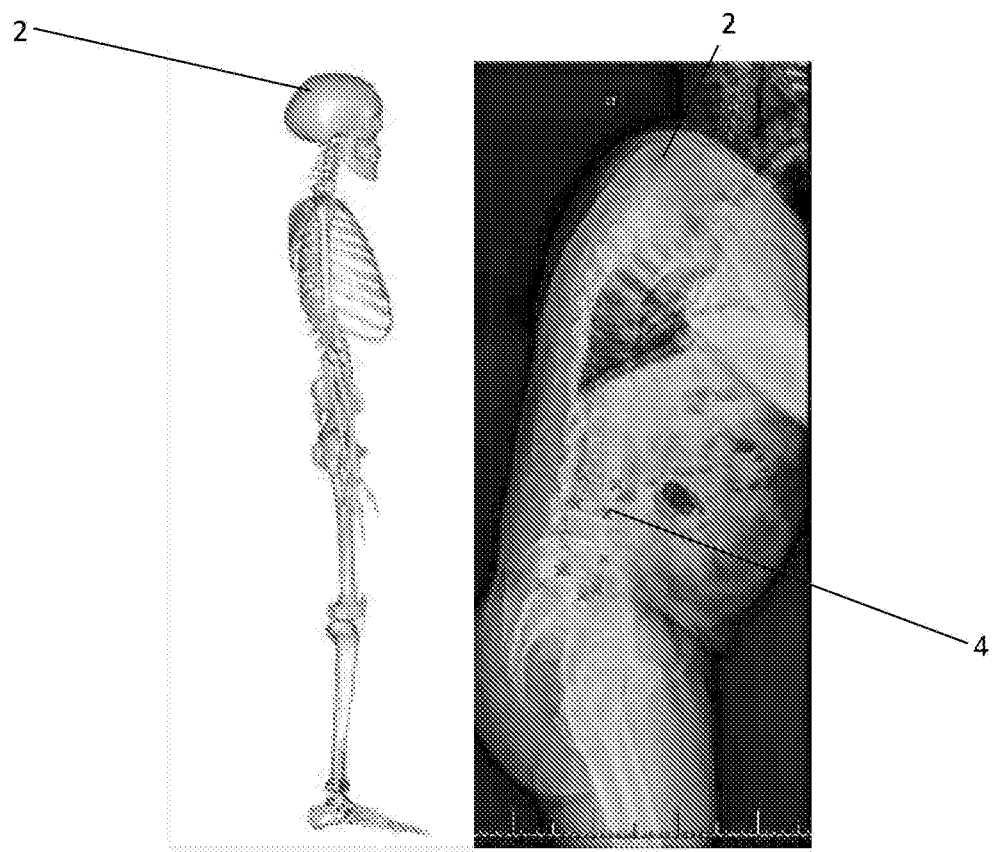
FIG. 2 illustrates a spine of a subject and an X-ray image of a subject.
Figure 8:
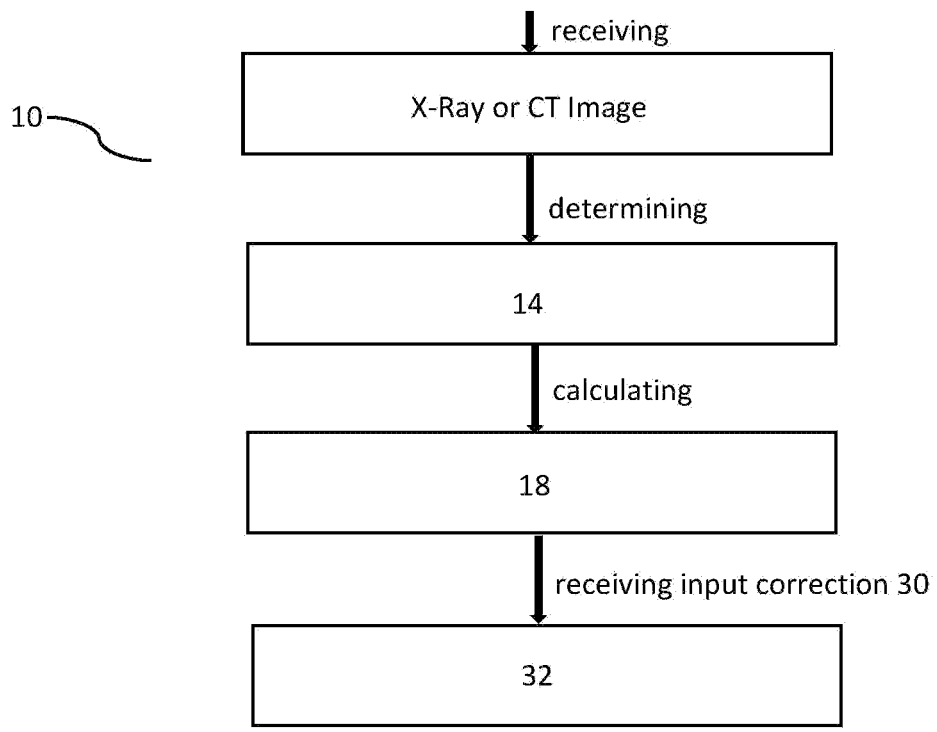
FIG. 8 illustrates steps of generating a musculoskeletal model of a subject according to an embodiment of the system.

In one embodiment, a system 10 for surgical planning and assessment of spinal deformity correction in a subject 2 includes a spinal imaging system 10 capable, or configured, to collect at least one digitized position 14 of one or more vertebral bodies 4 of the subject 2, shown in FIG. 1. It will be appreciated that the present discussion may be applicable to other structures, such as skull bodies and limb joints. The vertebral bodies 4 may be, for example, cervical, thoracic, lumbar, sacrum, or coccyx. The system 12 includes a control unit 16 containing software configured to receive, or collect, the digitized position 14, as shown in, for example, FIG. 8. The at least one digitized position 14 may be any number of positions that correspond to any number of locations, respectively, on the one or more vertebral bodies 4. For example, there may be at least two positions, at least four positions, at least eight positions, at least sixteen positions, or any number of positions therebetween. The at least one digitized position 14 may correspond to specific locations on the one or more vertebral bodies 4. In one embodiment, the positions 14 correspond to a corner, or multiple corners, of the vertebral bodies 4, as shown in FIG. 2. The control unit 16 may also be configured to collect information of the vertebral bodies 4, such as bone density, fractures, etc. The digitized positions 14 may be extracted from the subject 2 when the subject 2 is in a standing, lateral position.

Figure 6:
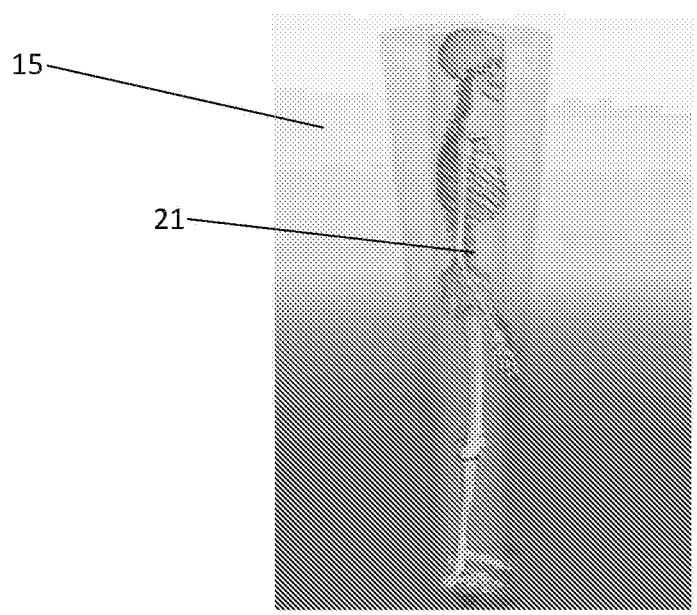
FIG. 6 illustrates a musculoskeletal model in an embodiment of the system.

The control unit 16 may collect the digitized position 14 from any data source of the subject 2 that depicts the vertebral bodies 4 in sufficient detail, including but not limited to, an X-ray image, a computed tomography image, a magnetic resonance imaging image, or biplanar X-ray image of the subject 2. The control unit 16 may contain image recognition software whereby the control unit 16 digitizes data provided, such as an X-ray image, a computed tomography image, a magnetic resonance imaging image, or biplanar X-ray image of the subject 2, and the control unit 16 may select digitized positions 14 based on output from the image recognition software. The image recognition software, by way of example, may process the image and identify and transmit the positions 14, such as the corners of the one or more vertebral bodies 4. In some embodiments, this processing and identification is automatic, while in other embodiments, a user manually selects or verifies the positions 14 from data provided to the control unit 16 such that the control unit 16 receives the digitized positions 14 from the user. In yet another embodiment, the digitized positions 14 are received digitally from a digital imaging component, such as a digital radiography system. The digitized positions 14 may be displayed using medical modeling system 15, such as the archiving and communication system (PACS), shown in FIG. 6.

In an embodiment of the system 10, the control unit 16 is configured to calculate, or determine, based on the at least one digitized position 14, an optimized posture 18 of the subject 2. As used herein, "optimized posture" refers to the posture that would be the desired, or ideal, clinical outcome for the subject 2, as for example, determined by a surgeon seeking to perform a spinal correction surgery on the subject 2 who is in need thereof. The control unit 16 may be configured to calculate the optimized posture 18 by parametric processing. In parametric processing, data regarding the at least one digitized position 14 may be compared to one or more predetermined optimized anatomical posture models 20. The predetermined optimized anatomical posture models 20 may not be patient-specific. The predetermined model 20 selected may be, for example, the predetermined model 20 that most closely corresponds to the anatomical characteristics of the subject 2. By way of example, the control unit 16 may be configured to include, or store, predetermined models 20 for subjects 2 of varying ages, gender and medical conditions (e.g., lordosis, kyphosis, scoliosis), and may select the predetermined model 20 most suitable for the subject 2. The at least one anatomical digitized positions 14 may be morphed, scaled, or adjusted, either manually or automatically, onto corresponding points 21 on the predetermined model 20. As discussed later, the predetermined model 20 may contain logic, inputs, and parameters for the predicting steps when determining optimized posture and/or simulated correction 24.

Figure 9:
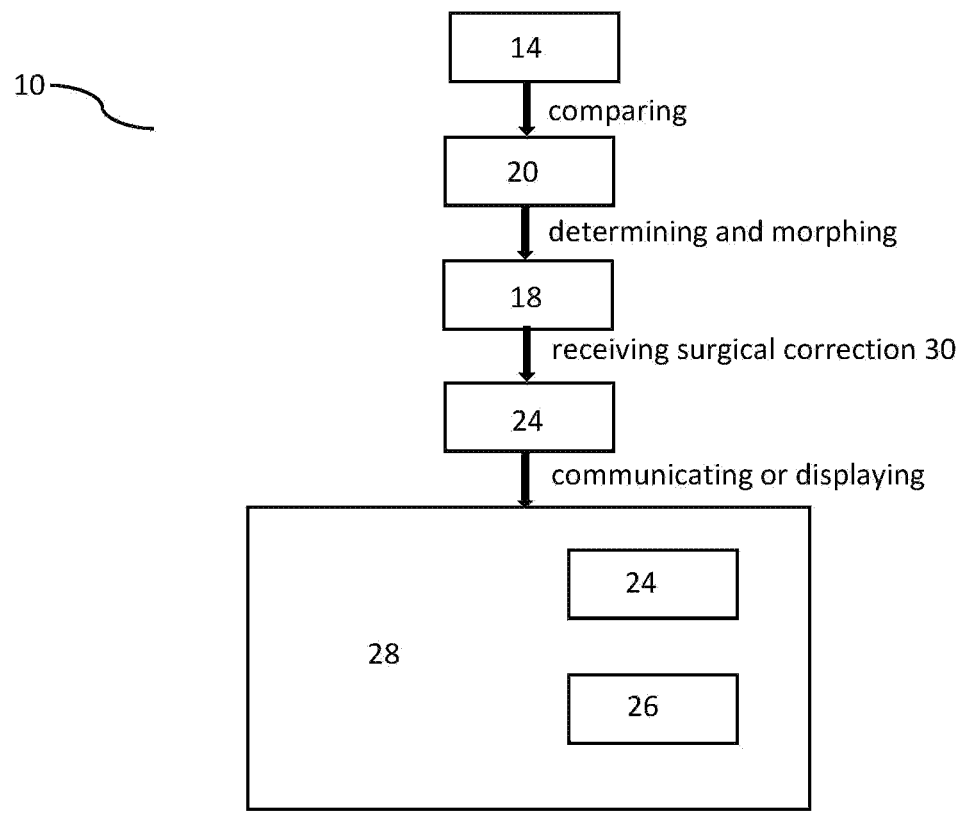
FIG. 9 illustrates steps of generating an output according to one embodiment of the system.

Based on the received at least one digitized position 14 of the one or more vertebral bodies 4, the control unit 16 is configured to predict, or determine, a simulated postoperative surgical correction 24 (i.e., predict how a surgical correction, such as a posterior lumbar interbody fusion or anterior lumbar interbody fusion, will affect the posture of the subject 2). The control unit 16 may be configured to determine, for example, the simulated postoperative surgical correction 24 that would result in, or close to, the optimized posture 18 for the subject 2. Based on the simulated postoperative surgical correction 24, the control unit 16 may be configured to determine, and display to a surgeon, a recommended surgical plan 26 to implement the predicted simulated postoperative surgical correction 24. The recommended surgical plan 26 may include, by way of example, information regarding surgical procedure, surgical approach, surgical technique, surgical instrument, and implant. The control unit 16 may communicate the predicted simulated postoperative spinal correction 24, and/or recommended surgical plan 26, to the user. By way of example and as shown in FIG. 9, the control unit 16 may be configured to communicate, or output, the predicted simulated postoperative surgical correction 24, corresponding to a variance from the calculated optimized posture 18. The communicated predicted simulated postoperative spinal correction 24, and/or recommended surgical plan 26 may be transmitted as an output 28. By way of example, the output 28 may be an image representation, a graphical display, or a numerical value.

Figure 10:
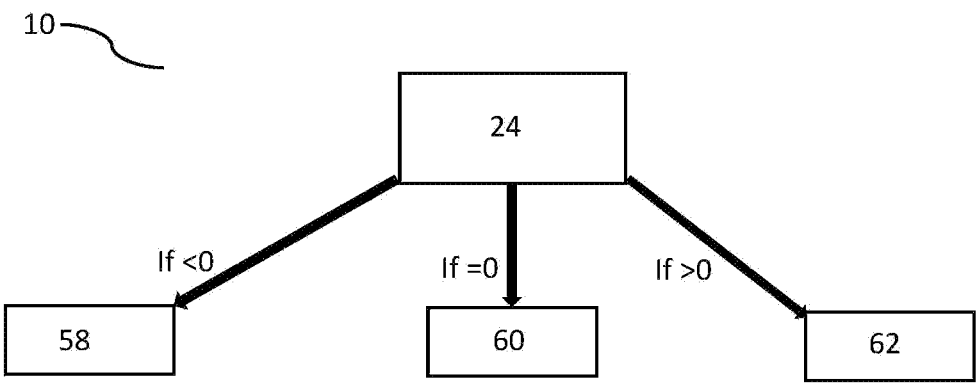
FIG. 10 illustrates steps of displaying results of a simulated surgical correction according to an embodiment of the system.

As illustrated in FIG. 10, in embodiments having output 28 as a numerical value, the output value of less than 0 may represent a predicted undercorrection 58 as compared to the optimized posture 18 and the output value of greater than 0 may represent an overcorrection 62 as compared to the optimized posture 18. A value of 0 may represent a desired, or optimal, spinal correction 60 that achieves the optimized posture 18 in the subject 2. Thus, the value of the output 28 may correspond to the variance of the predicted simulated postoperative surgical correction 24 with the optimized posture 18, with a higher degree positively correlating with higher variance. As used herein, "undercorrection" means that the predicted simulated postoperative surgical correction 24 is not able to fully correct the medical condition being corrected of the subject 2, and "overcorrection" means that that the predicted simulated postoperative surgical correction 24 overly corrects the medical condition being corrected of the subject 2. The value of the output 28 may correspond to any, or any combination, of measurements such as, a value of muscle activation in a patient, a value of kyphosis, a value of lordosis, and a value of Cobb angle.

Figure 11:
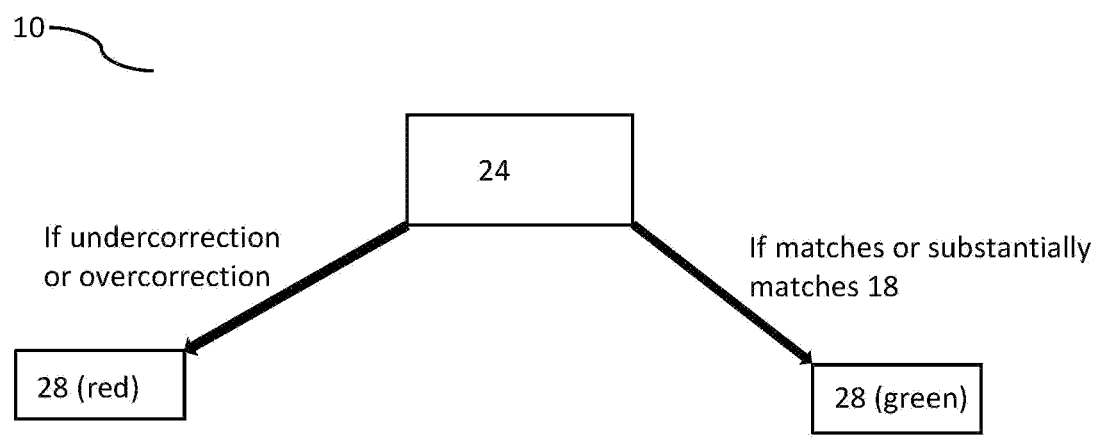
FIG. 11 illustrates steps of displaying results of a simulated surgical correction according to another embodiment of the system.

As described in FIG. 11, if the simulated postoperative surgical correction 24 results in a significant overcorrection or an undercorrection, the system 10 may display the output 28 in red, such as a red number or a red symbol. On the other hand, if the simulated postoperative surgical correction 24 results in an output 28 equal, or substantially equal, to the corresponding value in the optimized posture 18, the system 10 may display an output in green, such as a green number or a green symbol. The control unit 16 may be configured to transmit the outputs 28. Thus, the user (i.e., surgeon) can iteratively change an input plan or input parameters until the goal, such as optimal posture, is achieved.

By way of example, in the case of the subject 2 having Scoliosis, an X-ray image of the subject's 2 spine may be received by the control unit 16. The control unit 16 may automatically process the X-ray image to determine digitized positions 14, such as on points corresponding to corners of vertebrae bodies 4 of the subject 2. Using the digitized positions 14, the control unit 16 may calculate the optimized posture 18 of the subject 2. The control unit 16 may morph and scale the digitized positions 14 onto a predetermined model 20 to create a simulated, model 32 of the subject's 2 spine. The optimized posture 18 may have a spine with a Cobb angle of between 0 and 10 degrees, 2 and 8 degrees, or 2 and 6 degrees, or any combination of those values. The Scoliosis subject 2 may have a spinal Cobb of greater than 10 degrees, greater than 15 degrees, greater than 20 degrees, greater than 40 degrees, greater than 50 degrees, or greater than 60 degrees. The control unit 16 may communicate the Cobb value of the optimized posture 18 to the user. The control unit 16 may be configured to receive an input surgical correction 30, such as spinal fusion of specific vertebrae, to calculate the predicted simulated postoperative spinal correction 24, and/or recommended surgical plan 26. In some embodiments of the system 10, multiple plans 26 are recommended. If the optimized posture 18 has a Cobb angle of 0, and the simulated postoperative spinal correction 24 has a Cobb angle of 0, the control unit 16 would communicate to the user that the input surgical correction 30 achieves the optimized posture 18, such as by returning a value of 0. In contrast, if the optimized posture 18 has a Cobb angle of 0, and the simulated postoperative spinal correction 24 has a Cobb angle of −5 or +5, the control unit 16 would communicate to the user that the input surgical correction 30 results in an undercorrection of −5 or overcorrection of +5, respectively. Of course, the values that represent an undercorrection and overcorrection, such as degree and positivity, may be varied. In some embodiments, the control unit 16 may calculate and determine the predicted simulated postoperative surgical correction 24 to achieve the Cobb angle of 0 and determine a recommended surgical plan 26 that would result in the subject 2 having a Cobb angle of 0. The control unit 16 may be configured to communicate the simulated correction 24 and/or plan 26 to the user.

As can be appreciated, the system 10 may have numerous advantages. For example, the system 10 may provide the user with the optimized posture 18 of the subject 2. Using the optimized posture 18, the user may determine the optimal surgical plan 26 to achieve the optimized posture of the subject 2. In embodiments of the system 10 where the control unit 16 is configured to receive an input surgical correction 30 and output a simulated correction 24, the system 10 enables the user to remove the uncertainty, or "guesswork," as to the clinical outcome of a surgical correction. Advantageously, this feature of the system 10 would provide the user with information, such as whether the proposed surgical correction would result in an undercorrection of the medical condition being treated, that would allow the user to choose the surgical correction that would result in an efficacious clinical outcome for the subject 2 that avoids undercorrection or overcorrection. In embodiments where the system 10 predicts optimal correction 24 and/or plan 26 and communicates correction 24 and/or plan 26 to the user, the system 10 provides the user with an efficacious surgical correction that a surgeon can implement that avoids undercorrection or overcorrection. Indeed, the described system 10 is a new technological tool for improving surgical outcomes in subjects 2, particularly human subjects in need of and who receive spinal correction surgery.

Figure 3:
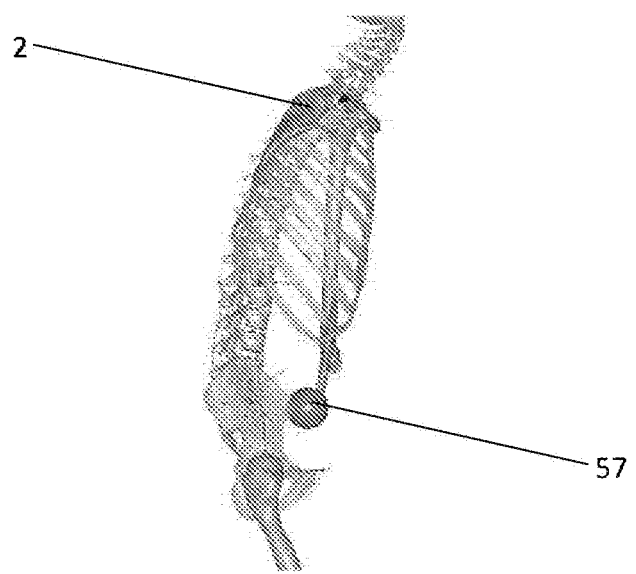
FIG. 3 illustrates a spine of a subject.
Figures 5A, 5B:
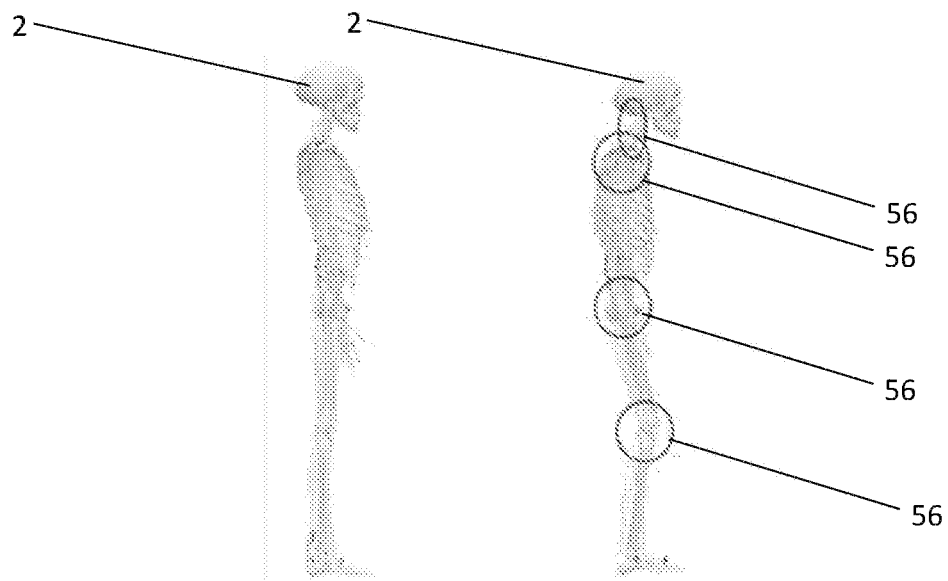
FIGS. 5A and 5B illustrate a model of a healthy spine and a kyphotic spine, respectively.

The control unit 16 is configured to process various values and factors, as well as contain various logics, to calculate optimized posture 18 and simulated postoperative surgical correction 24. For example, the control unit 16 may be configured to receive and process one or more compensation values 56 selected from the group consisting of: knee flexion, pelvic movement, ankle flexion, shoulder movement, lumbar movement, thoracic movement, cervical movement, spinal compensation, including ribs and neck, and a combination thereof, as shown in FIG. 5B. The control unit 16 may also be configured to receive and process center of mass migration 57. Knee flexion refers to joint angle between the bones of the limb at the knee joint. Knee flexion values may be, for example, between minus 10 and 150 degrees. Pelvic movement may include pelvic retroversion, pelvic anteversion, and pelvic tilt. Pelvic retroversion may be, for example, less than 50 degrees, less than 30 degrees, less than 25 degrees, less than 20 degrees, less than 15 degrees, less than 10 degrees, less than 5 degrees, or any range thereof. Center of mass migration 57, as shown in FIG. 3, refers to the point on the ground over which the mass of the subject 2 is centered, typically the center of mass migrations falls between the ankles of the subject 2. Ankle flexion refers to a joint angle between the bones of the limb at the ankle joint. These values may be taken from the subject 2 who is in a suitable position, such as standing, supine, and prone. Processing compensation values 56 and mass migration 57 is a technical problem much more difficult than that of processing a rigid skeleton with no compensation (FIG. 5A) that is overcome by the practicing of the present disclosure.

Figures 4A, 4B, 4C:
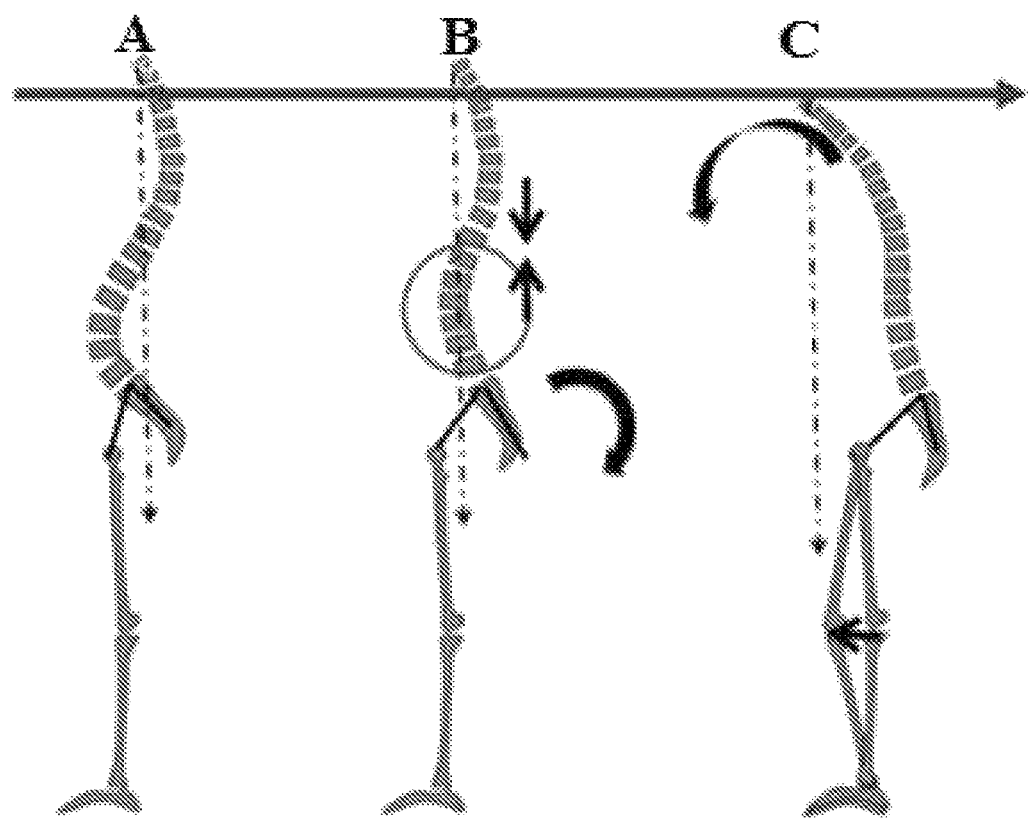
FIGS. 4A-4C illustrate various configurations of a spine.

FIG. 4A illustrates a non-degenerated spine with the spine in balance. FIG. 4B illustrates a generated spine and retroversion of the pelvis to compensate for the degeneration. FIG. 1C depicts a generated spine and flexion of the knee to compensate for such degeneration. Beneficially, the disclosed system and methods herein can account for these compensations, among other things, to produce a realistic and accurate model for surgical planning.

Figure 12:
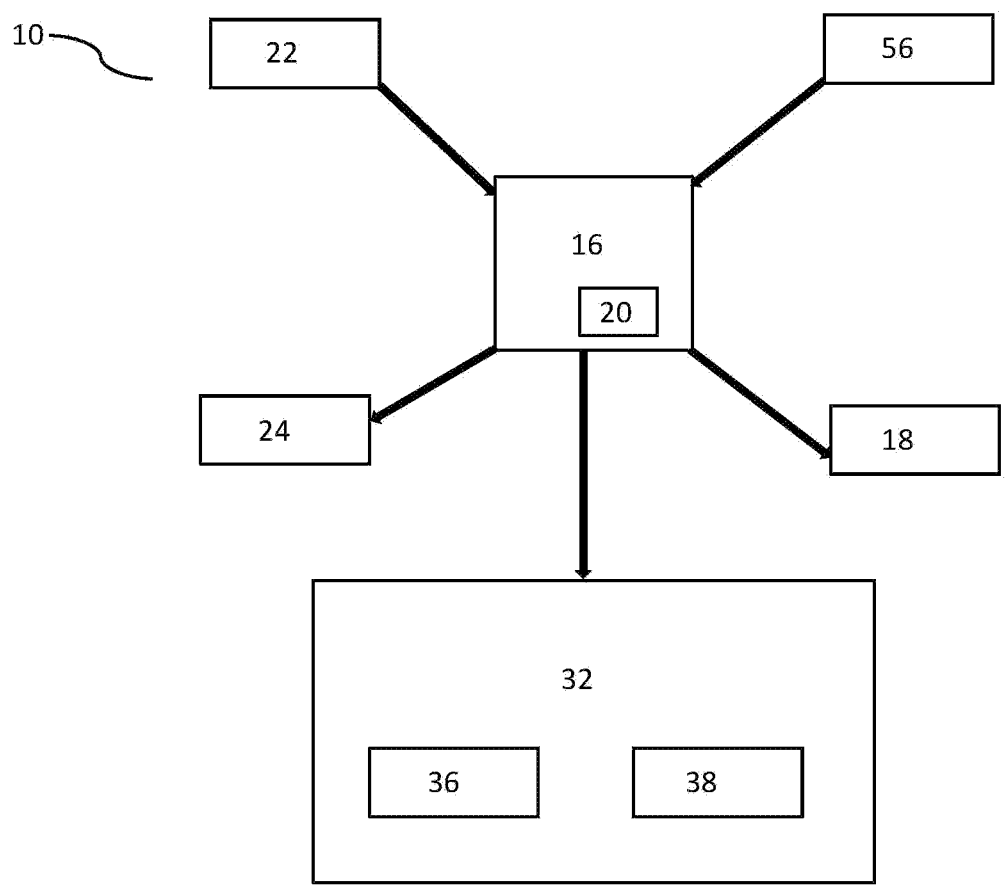
FIG. 12 illustrates an embodiment of the system.

As shown in FIG. 12, the control unit 16 may be configured to generate, or create, a musculoskeletal model 32 of the subject 2. The control unit 16 may be configured to compare the model 32 with the predetermined model 20 for the control unit's 16 calculation of the optimized posture 18. The control unit 16 may receive the digitized positions 14 to generate the musculoskeletal model 32 of the subject 2. The control unit 16 may also receive inputs 22, such as spinopelvic parameters, ligament parameters, joint kinematics, sagittal alignment measurements, spinal instability, and muscle recruitment criteria, and intervertebral fusion. As shown in FIGS. 7A-7C, the spinopelvic parameters may include parameters such as pelvic tilt (PT), sacral slope (SS), pelvic incidence (PI), sagittal vertical axis (SVA), lumbar lordosis, thoracic kyphosis, T1 pelvic angle, and combinations thereof. Further, the control unit 16 may input or use global alignment parameters such as global sagittal axis, three-dimensional parameters such as rotation and scoliosis, and cervical parameters. In some embodiments of the system 10, the spinopelvic parameters are used to assess, or determine, how far a subject is from a normal or optimum posture. The model 32 may also include muscle 36 force data or muscle activation data 38. The control unit 16 may be configured to use the inputs 22 to generate the musculoskeletal model 32 of the subject 2 and optimized posture 18 of the subject 2, which can include any, or all, of these parameters and inputs that reflect their respective values, or age-adjusted respective values, on the model 32. The control unit 16 may be configured to receive these inputs 22 manually or automatically. The control unit 16 may use these inputs 22 to compare and process in comparison to corresponding values on a predetermined model 20 in calculating optimized posture 18 and simulated surgical correction 24. Models 20, 32 may each have, or exclude, any parameter, logic, algorithm, input, or output discussed herein.

Figure 15:
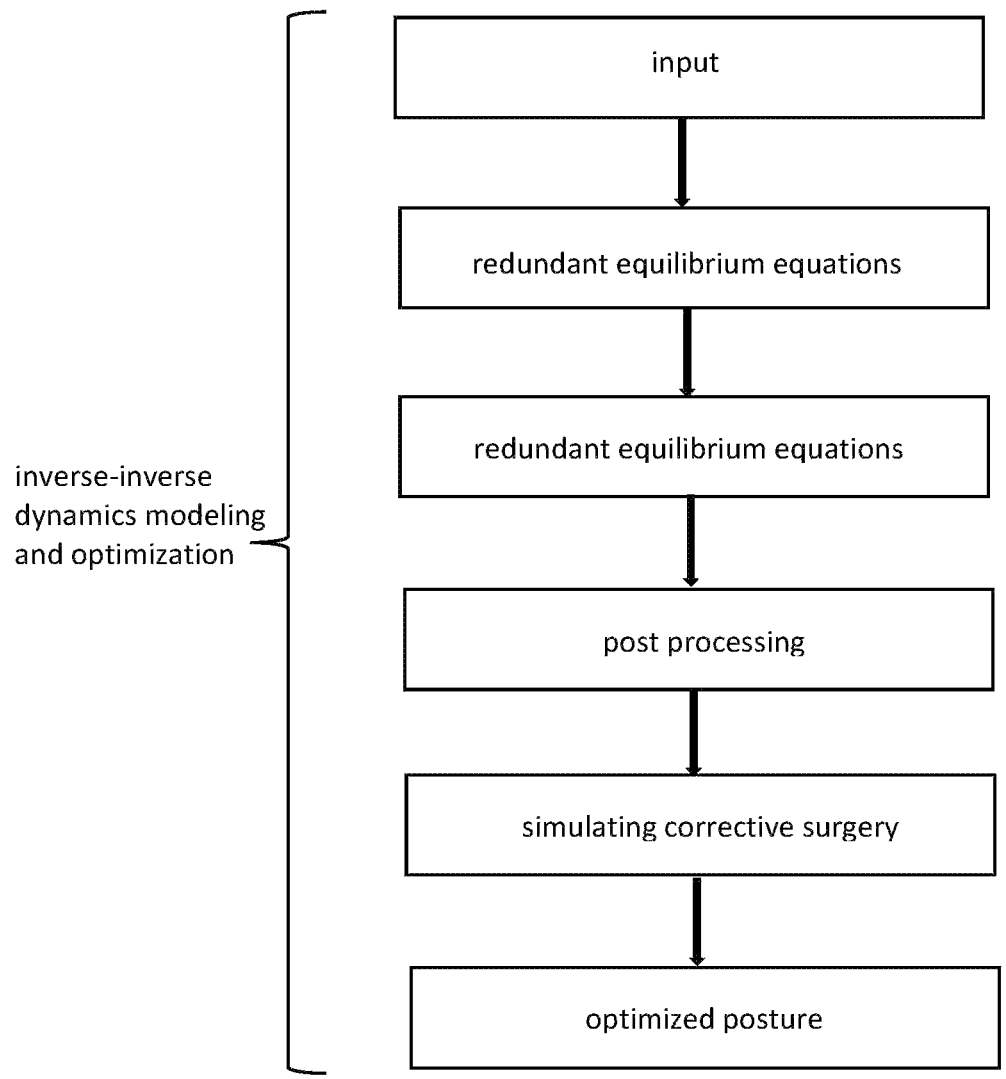
FIG. 15 illustrates steps of inverse-inverse dynamics processing and optimization according to an embodiment of the system.

The control unit 16 may process the digitized positions 14 by inverse-inverse dynamics modeling (FIG. 15). Advantageously, inverse-inverse dynamics modeling enables the system 10 to create a fluid model as opposed to a rigid model. Indeed, inverse-inverse dynamics modeling solves the technical problem of simulating how fluid joints and connectors (e.g, inputs 22) of subjects 2 affect a corrective surgery, particularly in instances where a rigid model would generate a model that would result in an undercorrection if implemented in a surgical correction. The control unit 16 may contain anatomical modeling software capable of, or configured to, simulate kinematics and muscular and joint loads in the full body for typical activities of a subject 2 and for fundamental human body motions. An example of such software is ANYBODY MODELING SYSTEM™ software, available from ANYBODY TECHNOLOGY™ of Aalborg, Denmark, configured to execute the inverse-inverse dynamics modeling. Moreover, the inverse-inverse dynamics model improves the functioning of control unit 16, as inverse-inverse dynamics enables control unit 16 to more accurately simulate the simulated surgical correction's interactions with anatomical properties of subject 2, especially properties specific to that subject 2, such as compensation, muscle elasticity, and joint elasticity.

Figure 13:
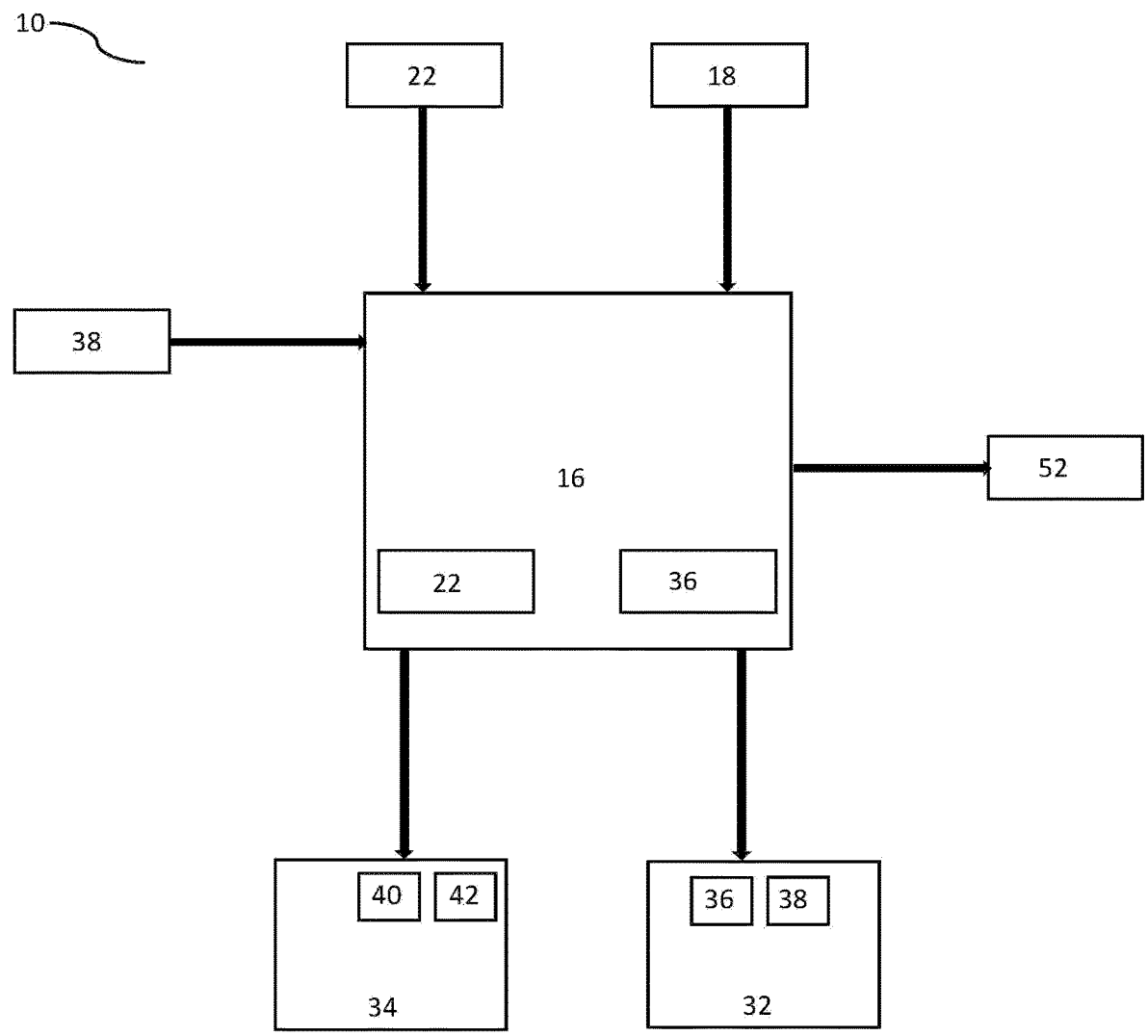
FIG. 13 illustrates yet another embodiment of the system.

As illustrated in FIG. 13, the control unit 16 may be configured to generate a sagittal curvature profile 34 based on the received digitized positions 14 and inputs 22. The profile 34 may be both a sagittal and coronal. The control unit 16 may morph (i.e., modify) the model 32 to match the profile 34. The musculoskeletal model data may be modified by scaling, adjusting positioning of the one or more vertebral bodies 4, morphing the simulated subject anatomical model 32, or combinations thereof.

Some, or all, of the inputs 22 may be predetermined, or manually or automatically received. The control unit 16 may be configured to apply logic parameters 36, such as that a subject 2 maintains a center of mass over the ankles; maintains a constant horizontal gaze; stands in a posture where postural muscle energy is minimized; has an arm position matching the patient during imaging (i.e., scaling); has no coronal plane deformity, or any combination of these logic parameters 36.

The control unit 16 may be configured to compare the calculated, or generated, musculoskeletal model 32 with predetermined musculoskeletal model data levels. Data from the calculated musculoskeletal model 32, such as muscle force data 36 or muscle activation data 38, may be used to calculate the simulated surgical correction 24 and communicated to a user through a display 52.

The control unit 16 may receive and process compensation values 56. In some embodiments, these values may be stored on the control unit 16. The control unit 16 may calculate compensation data 38, for example, hip compensation, ankle joint compensation, knee joint compensation, shoulder compensation, lumbar compensation, thoracic compensation, cervical compensation, or spinal compensation, including ribs and neck, to generate the model 32. Including compensation values 56 and/or compensation data 38 is particularly useful in some embodiments of the system 10, as the compensation values 56 and compensation data 38 considers that joints compensate for spinal changes, such as a degenerated spine. Thus, by including the values and data 56, 38, model 32 may be more accurately the subject's anatomy and compensation. The control unit 16 may also store predetermined compensation data 38 that is associated with the predetermined model 20.

The control unit 16 may also be configured to include a prediction of trunk muscle force 40 output and leg muscle force output 42 in the prediction of the simulated postoperative surgical correction 24. The trunk muscle force output may include cervical output, an erector spinae output, multifidi output, an obliques output, semispinalis output, an abdominal muscles output, or any combination thereof. The leg muscle force output includes a soleus output, a gastrocnemius output, a hip and knee flexors output, a hip and knee extensors output, a gluteus maximus output, a gluteus minimus output, or any combination thereof. These outputs 42, 44 may be communicated to a user through the display 52.

Figure 14A:
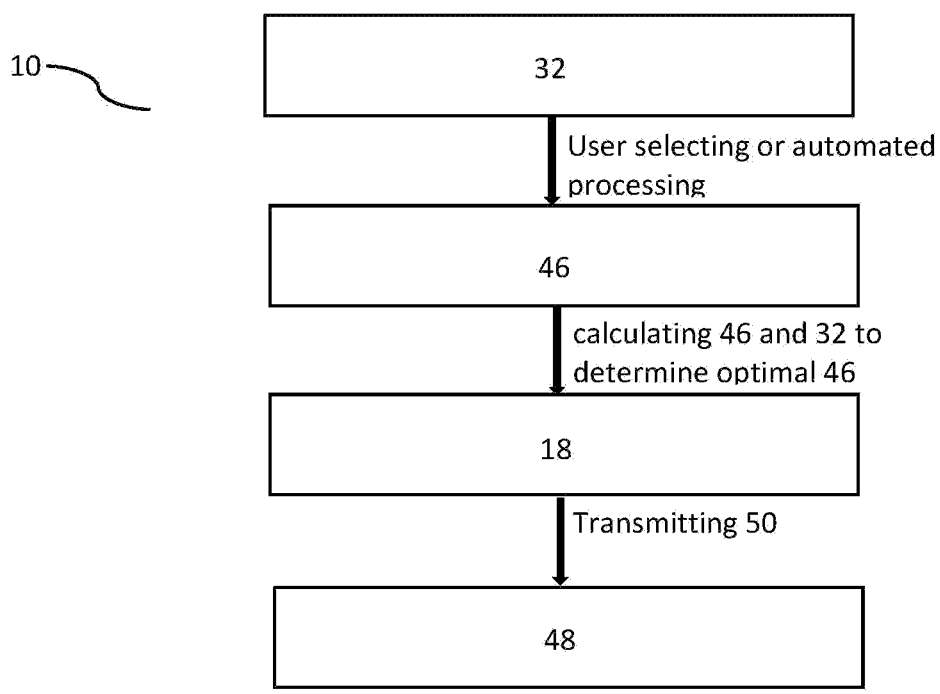
FIG. 14A illustrates steps for transmitting simulated implant data to an additive or subtractive manufacturing device according to an embodiment of the system.
Figure 16:
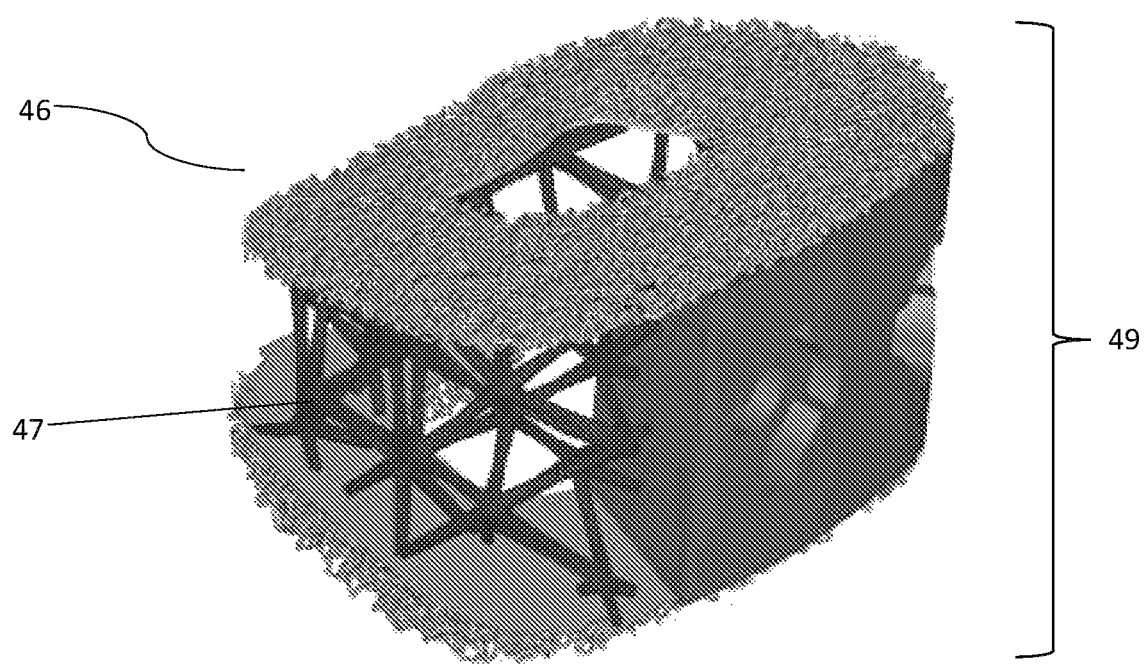
FIG. 16 illustrates a simulated implant according to an embodiment of the system.

As shown in FIG. 14A, in some embodiments of the system 10, the simulation of the postoperative surgical correction 24 includes simulating an implant 46 (FIG. 16) in the simulated model 32 of the subject 2. For example, a user of the system 10 may select, or design using engineering software, a simulated implant 46 to use in conjunction with the simulated postoperative surgical correction 24. The control unit 16 may be configured to receive input from the user for the location, orientation, type, size, and profile of the implant 46. In some embodiments of the system 10, the control unit 16 is configured to determine the simulated implant 46 that would achieve optimal posture 18 in the simulated corrective surgery 24. The determination may include the dimensions, location, orientation, type, size, and profile of the implant 46.

Figure 14B:
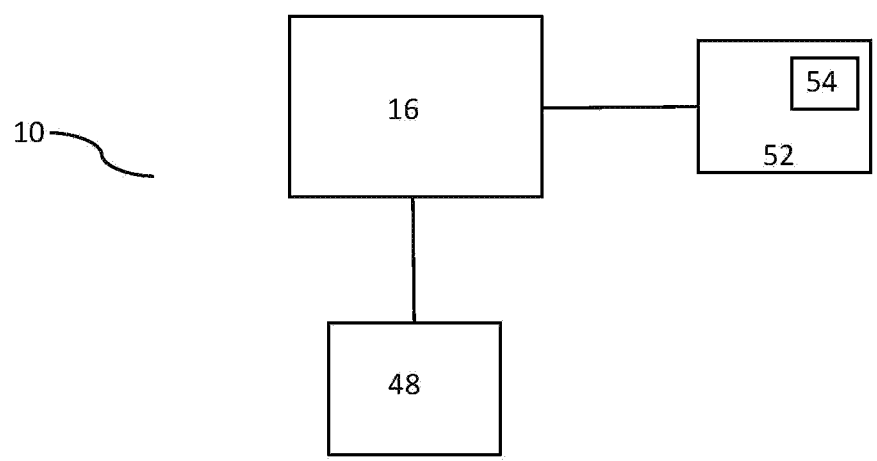
FIG. 14B illustrates an embodiment of the system having an additive or subtractive manufacturing device.

As illustrated in FIG. 14B, the system 10 may include a three dimensional printer (i.e., an additive manufacturing device or a subtractive manufacturing device) 48 in communication with the control unit 16. The three dimensional printer 48 may be configured to create, or partially create, the determined implant 46. Advantageously, this feature of the described disclosure allows for personalized surgical implants that are optimized for clinical benefit in the subject 2 to achieve optimized posture 18. The control unit 16 may be configured to transmit digital data 50 about the implant 46 for the printer 48 to manufacture the implant 46. The implant 46 may be designed on design software executed by the control unit 16 to achieve a desired structure and exported, for example as a .STL file, for preparation to be built with the three dimensional printer 48. The implant 46 may be designed to have a profile 49 to custom fit the morphology of vertebral body endplates of the subject 2, which may vary from subject to subject. The implant manufactured from simulated implant 46 may be constructed of any number, including multiple, suitable biocompatible material, such as titanium, titanium-alloy or stainless steel, surgical steel, or non-metallic compounds such as polymers.

In another aspect, a system 10 for surgical planning and assessment of spinal deformity correction in a subject 2 includes a spinal imaging device capable of collecting and transmitting to a control unit 16 at least one digitized position 14 of one or more vertebral bodies 4 of the subject 2. The control unit 16 is may be configured to receive the at least one digitized position 14 of the one or more vertebral bodies 4 of the subject 2, and calculate, based on morphing and scaling the at least one digitized position 14 onto a predetermined model 20 to form a simulated model 32, an optimized posture 18 for the subject 2.

The control unit 16 may be configured to execute software including optimization algorithms that tailor the profile of the implant 46 based upon loading conditions imparted to the implant 46, including: compression, shear, and torsion. The control unit 16 may include optimization algorithms that may be executed in order to produce a low-density, material efficient implant 46. This is accomplished by applying multiple, clinically-relevant, loading conditions to the implant 46 in the software program and allowing a finite element solver to optimize and refine, for example, a body lattice structure 47 of the implant 46.

The system 10 may include a display 52, such as a monitor, in communication with the control unit 16. The display 52 may be capable of receiving input from the user in addition to communicating feedback information to the user. By way of example (though it is not a necessity), a graphical user interface 54 (GUI) is utilized to enter data directly from the screen display 52.

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. A method comprising:
   obtaining at least one image of a subject, wherein the at least one image is any of (i) an X-ray image, (ii) a computed tomography image, (iii) a magnetic resonance imaging image, (iv) a biplanar X-ray image, or (v) any combination of (i)-(iv);
   obtaining, from the at least one image, a set of anatomical positions of at least two vertebrae of the subject;
   determining a model of the subject based on the set of anatomical positions, wherein the model defines a sagittal curvature profile, a coronal curvature profile, and one or more spinal parameters;
   receiving one or more simulated spinal correction inputs corresponding to a surgical procedure;
   predicting a simulated postoperative surgical correction for the subject based on the one or more simulated spinal correction inputs and the model;
   determining a surgical plan for the subject based on the simulated postoperative surgical correction;
   providing the surgical plan via a display;
   designing a simulated spinal implant for use in conjunction with the simulated postoperative surgical correction;
   manufacturing a personalized spinal implant configured to be implanted in the subject, the manufacturing being based on the simulated spinal implant; and
   providing the personalized spinal implant for implantation into the subject.

2. The method of claim 1, wherein obtaining, from the at least one image, the set of anatomical positions of the at least two vertebrae of the subject includes:
   receiving digitized positions that correspond to at least one position on each of the at least two vertebrae in the at least one image.

3. The method of claim 1, wherein the simulated postoperative surgical correction maintains a center of mass of the subject over the ankles of the subject.

4. The method of claim 1, further comprising:
   calculating an optimized posture for the subject based on a comparison of the model and one or more predetermined models.

5. The method of claim 1, wherein predicting the simulated postoperative surgical correction includes predicting one or both of (v) postoperative muscle force data and (vi) postoperative muscle activation data.

6. The method of claim 1, wherein the at least one image is of the subject in a standing lateral position.

7. The method of claim 1, wherein designing the simulated spinal implant includes receiving input from a user for a location and a size of the simulated spinal implant.

8. The method of claim 1, wherein the obtaining the set of anatomical positions of a patient from the at least one image includes applying image recognition software to the at least one image.

9. The method of claim 1, wherein the model is a musculoskeletal model.

10. The method of claim 1, wherein determining the model comprises using inverse-inverse dynamics modeling.

11. The method of claim 1, wherein the model includes joint kinematics.

12. The method of claim 1, wherein predicting the simulated postoperative surgical correction includes a prediction of simulated anterior lumbar interbody fusion surgery.

13. The method of claim 1, wherein the one or more simulated spinal correction inputs includes at least one of sagittal alignment and muscle recruitment criteria.

14. The method of claim 1, further comprising:
outputting a value, based on the simulated postoperative surgical correction, corresponding to a variance from an optimal posture.

15. The method of claim 1, further comprising:
providing a classification of the surgical plan as representing an overcorrection or an undercorrection.

16. The method of claim 1, further comprising:
receiving a modification of the surgical plan;
modifying the surgical plan based on the modification to form a modified surgical plan; and
providing the modified surgical plan via the display.

17. The method of claim 1, wherein the one or more spinal parameters include one or more parameters selected from the group consisting of: a pelvic tilt value, a pelvic incidence value, a sagittal vertical axis value, and a lumbar lordosis value.

18. The method of claim 1, further comprising, implanting the personalized spinal implant in the subject.

19. A method comprising:
obtaining at least one image of a subject, wherein the at least one image is an X-ray image, a computed tomography image, a magnetic resonance imaging image, or a biplanar X-ray image;
obtaining, from the at least one image, a set of anatomical positions of at least two vertebrae of the subject;
determining a musculoskeletal model of a subject based on the set of anatomical positions, wherein the musculoskeletal model defines muscle force data, a sagittal curvature profile, a coronal curvature profile, and one or more spinal parameters;
receiving one or more simulated spinal correction inputs corresponding to a surgical procedure;
predicting a simulated postoperative surgical correction for the subject based on the received one or more simulated spinal correction inputs and the musculoskeletal model;
providing the determined surgical plan via a display;
communicating muscle force data associated with the determined surgical plan to a user;
determining a surgical plan for the subject based on the predicted simulated postoperative surgical correction;
designing a simulated spinal implant for use in conjunction with the simulated postoperative surgical correction;
manufacturing a personalized spinal implant configured to be implanted in the subject, the manufacturing being based on the designed simulated implant; and
providing the personalized spinal implant for implantation into the subject.

20. A method comprising:
obtaining at least one image of a subject, wherein the at least one image is an X-ray image, a computed tomography image, a magnetic resonance imaging image, or a biplanar X-ray image;
obtaining, from the at least one image, a set of anatomical positions of at least two vertebrae of the subject;
determining a model of the subject based on the set of anatomical positions, wherein the model defines a sagittal curvature profile, a coronal curvature profile, and one or more spinal parameters;
receiving one or more simulated spinal correction inputs corresponding to a surgical procedure;
predicting an effect the surgical procedure will have on a postoperative posture of the subject;
providing the determined surgical plan via a display;
determining a surgical plan for the subject based on the predicted effect of the surgical procedure on the postoperative posture of the subject;
designing a simulated spinal implant for use in conjunction with the surgical procedure;
manufacturing a personalized spinal implant configured to be implanted in the subject, the manufacturing being based on the designed simulated implant; and
providing the personalized spinal implant for implantation into the subject.

* * * * *